(12) United States Patent
Greaves et al.

(10) Patent No.: US 7,744,658 B2
(45) Date of Patent: Jun. 29, 2010

(54) INDOLE-DERIVED STYRYL DYE COMPRISING AN ALKYLENE LINKER, A DYE COMPOSITION COMPRISING THIS DYE, AND A PROCESS FOR LIGHTENING KERATIN MATERIALS USING THIS DYE

(75) Inventors: Andrew Greaves, Montevrain (FR); Nicolas Daubresse, la Celles St Cloud (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 12/234,072

(22) Filed: Sep. 19, 2008

(65) Prior Publication Data

US 2009/0089939 A1    Apr. 9, 2009

Related U.S. Application Data

(60) Provisional application No. 60/960,612, filed on Oct. 5, 2007.

(30) Foreign Application Priority Data

Sep. 21, 2007    (FR) .................................. 07 57773

(51) Int. Cl.
*D06P 1/00* (2006.01)
(52) U.S. Cl. ........................ 8/636; 8/565; 8/568; 8/648
(58) Field of Classification Search ..................... 8/405, 8/435, 568, 648, 636, 565
See application file for complete search history.

(56) References Cited

U.S. PATENT DOCUMENTS

| | | | |
|---|---|---|---|
| 2,904,385 A | 9/1959 | Roger et al. | |
| 4,823,985 A | 4/1989 | Grollier et al. | |
| 5,944,360 A | 8/1999 | Crapart et al. | |
| 7,147,673 B2 | 12/2006 | Plos et al. | |
| 7,150,764 B2 | 12/2006 | Plos et al. | |
| 7,186,278 B2 | 3/2007 | Plos et al. | |
| 7,192,454 B2 | 3/2007 | Plos et al. | |
| 7,195,650 B2 | 3/2007 | Plos et al. | |
| 7,195,651 B2 | 3/2007 | Plos et al. | |
| 7,198,650 B2 | 4/2007 | Pourille-Grethen et al. | |
| 7,204,860 B2 | 4/2007 | Plos et al. | |
| 7,208,018 B2 | 4/2007 | Gourlaouen et al. | |
| 7,217,296 B2 | 5/2007 | Pastore et al. | |
| 7,250,064 B2 | 7/2007 | Plos et al. | |
| 7,261,744 B2 | 8/2007 | Gourlaouen et al. | |
| 7,276,086 B2 | 10/2007 | Gourlaouen et al. | |
| 7,303,589 B2 | 12/2007 | Greaves et al. | |
| 7,377,946 B2 | 5/2008 | Gourlaouen et al. | |
| 7,488,354 B2 | 2/2009 | Daubress et al. | |
| 7,531,008 B2 | 5/2009 | Lagrange | |
| 7,544,215 B2 | 6/2009 | Speckbacher et al. | |
| 2003/0176316 A1 | 9/2003 | Whitehead et al. | |
| 2004/0253757 A1 | 12/2004 | Gourlaouen et al. | |
| 2005/0031563 A1 | 2/2005 | Gourlaouen et al. | |
| 2007/0143936 A1* | 6/2007 | Lagrange ...................... 8/405 |
| 2007/0231940 A1 | 10/2007 | Gourlaouen et al. | |
| 2009/0049621 A1 | 2/2009 | Greaves et al. | |
| 2009/0089939 A1 | 4/2009 | Greaves et al. | |
| 2009/0126125 A1 | 5/2009 | Greaves et al. | |
| 2009/0126755 A1 | 5/2009 | Guerin et al. | |

FOREIGN PATENT DOCUMENTS

| | | |
|---|---|---|
| BE | 669 934 | 1/1966 |
| EP | 0 860 636 | 8/1998 |
| EP | 1 464 321 | 10/2004 |
| EP | 1 464 324 | 10/2004 |
| EP | 1 647 580 | 4/2006 |
| EP | 1 464 323 B1 | 12/2006 |
| EP | 1 792 605 A | 6/2007 |
| EP | 2 001 960 | 12/2008 |
| EP | 2 004 757 | 12/2008 |
| EP | 2 018 847 | 1/2009 |
| EP | 2 062 945 | 5/2009 |
| FR | 1 156 407 | 5/1958 |
| FR | 2 586 913 | 3/1987 |
| FR | 2 830 189 A1 | 4/2003 |
| FR | 2 830 194 A1 | 4/2003 |
| FR | 2 850 271 A1 | 7/2004 |
| FR | 2 921 381 | 3/2009 |
| FR | 2 921 377 | 6/2009 |

(Continued)

OTHER PUBLICATIONS

STIC Seach Report dated Apr. 23, 2009.*

(Continued)

*Primary Examiner*—Eisa B Elhilo
(74) *Attorney, Agent, or Firm*—Finnegan, Henderson, Farabow, Garrett & Dunner, LLP

(57) ABSTRACT

The disclosure relates to the dyeing of keratin materials using indole-derived styryl dyes comprising an alkylene linker. Disclosed herein is a dye composition comprising an indole-derived styryl dye comprising an alkylene linker, and a dyeing process with, for example, a lightening effect on keratin materials such as hair, using said composition. Disclosed herein are novel indole-derived styryl dyes comprising an alkylene linker and the uses thereof in lightening keratin materials. This composition makes it possible to obtain a coloring with a lightening effect which can be resistant and visible on dark keratin fibers.

12 Claims, No Drawings

FOREIGN PATENT DOCUMENTS

| | | |
|---|---|---|
| GB | 2 143 541 | 2/1985 |
| GB | 2 180 215 | 3/1987 |
| WO | WO 96/41173 | 12/1996 |
| WO | WO 99/51194 | 10/1999 |
| WO | WO 03/28685 | 4/2003 |
| WO | WO 2004/091473 | 10/2004 |
| WO | WO 2004/091556 | 10/2004 |
| WO | WO 2005/004822 | 1/2005 |
| WO | WO 2005/075574 | 8/2005 |
| WO | WO 2005/097051 | 10/2005 |
| WO | WO 2006/060533 | 6/2006 |
| WO | WO 2006/134043 | 12/2006 |
| WO | WO 2006/136617 | 12/2006 |
| WO | WO 2007/025889 | 3/2007 |
| WO | WO 2007/039527 | 4/2007 |
| WO | WO 2007/110537 | 10/2007 |
| WO | WO 2007/110539 | 10/2007 |
| WO | WO 2007/110542 | 10/2007 |
| WO | WO 2009/037324 | 3/2009 |
| WO | WO 2009/037348 | 3/2009 |
| WO | WO 2009/037350 | 3/2009 |
| WO | WO 2009/037385 | 3/2009 |
| WO | WO 2009/040354 | 4/2009 |
| WO | WO 2009/040355 | 4/2009 |

OTHER PUBLICATIONS

French Search Report for FR 0757773 dated Jul. 7, 2008.
IP.com accessible on Oct. 13, 2005.
Ashwell et al., "Improved Molecular Rectification from Self-Assembled Monolayers of a Sterically Hindered Dye," *Journal of the American Chemical Society*, vol. 127, No. 46, (2005), pp. 16238-16244.
Ashwell et al., "Induced Rectification from Self-Assembled Monolayers of Sterically Hindered-Bridged Chromophores," *Journal of Materials Chemistry*, vol. 15, No. 11, (2005), pp. 1160-1166.
Ashwell et al., "Molecular Rectification: Self-Assembled Monolayers of a Donor Acceptor Chromophore Connected via a Truncated Bridge," *Journal of Materials Chemistry*, vol. 13, No. 12, (2003), pp. 2855-2857.
Copending U.S. Appl. No. 12/233,955, filed Sep. 19, 2008.
Copending U.S. Appl. No. 12/234,001, filed Sep. 19, 2008.
Copending U.S. Appl. No. 12/234,135, filed Sep. 19, 2008.
Copending U.S. Appl. No. 12/282,586, filed Sep. 11, 2008.
Copending U.S. Appl. No. 12/293,684, filed Sep. 19, 2008.
Copending U.S. Appl. No. 12/293,723, filed Sep. 19, 2008.
Copending U.S. Appl. No. 12/293,955, filed Sep. 22, 2008.
English language Abstract of EP 2 001 960, dated Dec. 17, 2008.
English language Abstract of EP 2 004 757, dated Dec. 24, 2008.
English language Abstract of EP 2 018 847, dated Jan. 28, 2009.
English language Abstract of EP 2 062 945, dated May 27, 2009.
English language Abstract of FR 2 921 377, dated Jun. 17, 2009.
English language Abstract of FR 2 921 381, dated Mar. 27, 2009.
English language Abstract of WO 2007/110537, dated Oct. 4, 2007.
English language Abstract of WO 2007/110539, dated Oct. 4, 2007.
English language Abstract of WO 2007/110542, dated Oct. 4, 2007.
European Search Report for EP 08 16 4735, dated May 19, 2009.
French Search Report for FR 07/57753, dated Aug. 4, 2008.
French Search Report for FR 07/57755, dated Jul. 30, 2008.
French Search Report for FR 07/57778, dated Aug. 20, 2008.
International Search Report for PCT/FR2007/050997, dated Jun. 19, 2008.
International Search Report for PCT/FR2007/051003, dated Feb. 19, 2008.
International Search Report for PCT/FR2007/051005, dated May 6, 2008.
International Search Report for PCT/FR2007/051008, dated Feb. 5, 2008.
Kajikawa et al., "Preparation and Optical Characterization of Hemicyanine Self-Assembled Monolayer on Au Substrate," *Molecular Crystals and Liquid Crystals Science and Technology*, vol. 370, (2001), pp. 277-283.
Naraoka R. et al., "Nonlinear Optical Property of Hemicyanine Self-Assembled Monolayers on Gold and its Absorption Kinetics Probed by Optical Second-Harmonic Generation and Surface Plasmon Resonance Spectroscopy," *Chemical Physics Letters*, vol. 362, No. 1-2, (2002), pp. 26-30.
Notice of Allowance mailed Jan. 11, 2010, in co-pending U.S. Appl. No. 12/233,955.
Notice of Allowance mailed Jan. 11, 2010, in co-pending U.S. Appl. No. 12/234,001.
Notice of Allowance mailed May 4, 2009, in co-pending U.S. Appl. No. 12/234,135.
Notice of Allowance mailed Sep. 3, 2009, in co-pending U.S. Appl. No. 12/234,135.
Okawa et al., "Synthesis and Characterization of an Alkanethiol Thin Film Containing a Hemicyanine Dye," *Molecular Crystals and Liquid Crystals*, vol. 377, (2002), pp. 137-140.
STIC Search Report for U.S. Appl. No. 12/233,955, dated Dec. 9, 2009.
STIC Search Report for U.S. Appl. No. 12/234,001, dated Dec. 7, 2009.
STIC Search Report dated Apr. 27, 2009, for U.S. Appl. No. 12/234,135.
Tsuboi et al., "Formation of Merocyanine Self-Assembled Monolayer and its Nonlinear Optical Properties Probed by Second-Harmonic Generation and Surface Plasmon Resonance," *Japanese Journal of Applied Physics*, vol. 42, No. 2A, (2003), pp. 607-613.
Wang et al., "Synthesis and Fluorescence Properties of Triad Compounds with Aromatic Sulfur Bridges," *Dyes and Pigments*, vol. 51, No. 2-3, (2001), pp. 127-136.
Wang et al., "Synthesis and Luminescence Properties of Triad Compounds with a Disulfide Bridge," *Dyes and Pigments*, vol. 54, No. 3, (2002), pp. 265-274.

* cited by examiner

INDOLE-DERIVED STYRYL DYE COMPRISING AN ALKYLENE LINKER, A DYE COMPOSITION COMPRISING THIS DYE, AND A PROCESS FOR LIGHTENING KERATIN MATERIALS USING THIS DYE

This application claims benefit of U.S. Provisional Application No. 60/960,612, filed Oct. 5, 2007, the contents of which are incorporated herein by reference. This application also claims benefit of priority under 35 U.S.C. § 119 to French Patent Application No. FR 0757773, filed Sep. 21, 2007, the contents of which are also incorporated herein by reference.

The present disclosure relates to the dyeing of keratin materials using indole-derived styryl dyes comprising an alkylene linker.

It is well known to dye keratin fibers, such as human keratin fibers, by direct dyeing. The process conventionally used in direct dyeing comprises applying to the keratin fibers direct dyes which are colored or coloring molecules having an affinity for the fibers, allowing them to diffuse, and then rinsing the fibers.

The direct dyes which are conventionally used are, for example, dyes of the nitrobenzene type, anthraquinone dyes, nitropyridine dyes, or dyes of the azo, xanthene, acridine, azine, or triarylmethane type.

Moreover, the coloring of keratin fibers using these conventional direct dyes does not make it possible to significantly lighten keratin fibers.

The lightening of the color of keratin fibers, such as dark keratin fibers, to lighter shades, by optionally modifying the shade thereof, constitutes an important demand.

Conventionally, in order to obtain a lighter coloring, a chemical bleaching process is used. This process comprises treating the keratin fibers, such as the hair, with a strong oxidizing system, generally composed of hydrogen peroxide, possibly in combination with persalts, generally in an alkaline medium.

This bleaching system has the drawback of damaging the keratin fibers, such as the hair, and of detrimentally affecting their cosmetic properties. The fibers in fact have a tendency to become rough, more difficult to disentangle, and more brittle. Furthermore, the lightening or the bleaching of keratin fibers with oxidizing agents is incompatible with the treatments for modifying the shape of said fibers, for instance, in hair straightening treatments.

Another lightening technique comprises applying fluorescent direct dyes to dark hair. This technique, described for example, in International Patent Application Publication Nos. WO 03/028685 and WO 2004/091473, and European Patent No. EP 1792605, makes it possible to retain the quality of the keratin fiber during the treatment. However, some of these fluorescent direct dyes do not exhibit satisfactory performance levels, for example, in terms of color uptake into the keratin fiber, selectivity, stability, fastness, and solubility in the cosmetic dyeing media.

One aspect of the present disclosure is to provide new systems for dyeing keratin materials, for example human keratin fibers such as the hair, which do not have the drawbacks of the existing bleaching processes.

In another aspect of the present disclosure is to dye keratin materials chromatically and in a manner which is persistent with respect to outside attacks. Another aspect of the present disclosure is to provide direct dyeing systems for obtaining lightening effects, such as on naturally or artificially dark keratin fibers, which are resistant to successive shampooing operations, which do not damage the keratin fibers, and which do not detrimentally affect their cosmetic properties.

These aims can be achieved with the present disclosure, a subject of which is a process for dyeing keratin materials, for example keratin fibers, for instance, human keratin fibers such as the hair, for example, dark hair, comprising applying, to the keratin materials, a dye composition comprising, in a cosmetically acceptable medium, at least one indole-derived styryl dye comprising an alkyl or alkylene linker, chosen from the dyes of formula (I):

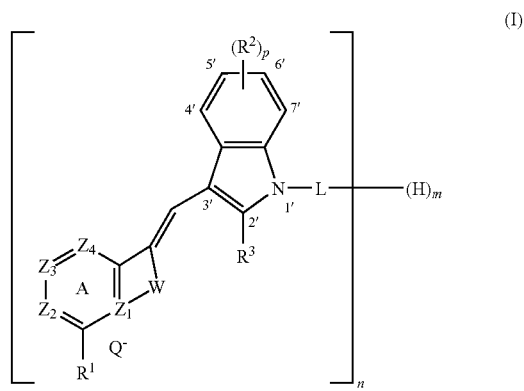

the organic or mineral acid salts thereof, optical isomers and geometric isomers thereof, and the solvates thereof, such as hydrates:

wherein:
- n is an integer ranging from 1 to 2;
- m is an integer ranging from 0 to 1;
- p is chosen from an integer ranging from 0 to 4;
- $Q^-$ is an anionic counterion;
- W is chosen from a $(C_2-C_3)$alkylene and a $(C_2-C_3)$alkenylene chain optionally substituted with at least one $(C_1-C_4)$alkyl or aryl group; for example, W is an unsubstituted $(C_2-C_3)$alkylene chain;
- $Z_1$ is a carbon atom or a nitrogen atom $N^+$ which is quaternized;
- $Z_2$, $Z_3$, and $Z_4$, which may be identical or different, are chosen from a nitrogen atom, a $CR^4$, and a $N^+R^5$ group; with the proviso that only one quaternized nitrogen atom $N^+$ or $N^+R^5$ may be present in the aromatic ring A;
- $R^1$, $R^2$, and $R^4$, which may be identical or different, are chosen from a hydrogen atom, a halogen atom, a (di)$(C_1-C_6)$(alkyl)amino, a cyano, a hydroxyl, a (poly)halo$(C_1-C_6)$alkyl such as trifluoromethyl, a acyl$(C_1-C_4)$(alkyl)amino, a $(C_1-C_6)$alkoxy, a $(C_1-C_6)$alkylthio, a (poly)hydroxy$(C_2-C_6)$alkoxy, a $(C_1-C_6)$alkylcarbonyloxy, a $(C_1-C_6)$alkoxycarbonyl, a $(C_1-C_6)$alkylcarbonylamino, a (di)$(C_1-C_4)$(alkyl)aminocarbonyl, a $(C_1-C_6)$alkylsulfonyl$(C_1-C_4)$(alkyl)amino, a (di)$(C_1-C_4)$(alkyl)aminosulfonyl group, and a $(C_1-C_6)$alkyl group optionally substituted with a group chosen from $(C_1-C_6)$alkoxy, hydroxyl, and (di)$(C_1-C_6)$(alkyl)amino; or, when p is an integer greater than or equal to 2, two contiguous radicals $R^2$ form, together with the carbon atoms to which they are attached, a benzo ring;
- $R^3$ is chosen from a hydrogen atom, an optionally substituted $(C_1-C_6)$alkyl group, a (di)$(C_1-C_6)$(alkyl)amino group, an aryl group such as phenyl, and a heterocycloalkyl group which is optionally substituted, such as morpholino, piperidino, piperazino optionally substituted with a $(C_1-C_3)$alkyl group;

$R^5$ is chosen from an optionally substituted $(C_1-C_6)$alkyl group and an aryl$(C_1-C_6)$alkyl; for example, $R^5$ is a $(C_1-C_4)$alkyl group such as methyl or ethyl;

L is chosen from a σ bond and an optionally substituted $C_1-C_{20}$ divalent hydrocarbon-based chain, optionally interrupted i) with at least one divalent group or combination thereof chosen from: —N(R)—; —N$^+$(R)(R°)—, An$^-$; —O—; —C(O)—, and —S(O)$_2$—, wherein R and R°, which may be identical or different, are chosen from a hydrogen, a $(C_1-C_4)$alkyl, a hydroxy$(C_1-C_4)$alkyl, and an amino$(C_1-C_4)$alkyl radical, and An$^-$ is an anionic counterion, or ii) with a cationic heterocycle or cationic heteroaryl Het$^+$, An$^-$, wherein An$^-$ is an anionic counterion and Het$^+$ is chosen from a saturated or unsaturated heterocycle comprising from 5 to 10 members and a heteroaryl comprising from 5 to 10 members, such as imidazolium, pyridinium, piperazinium, piperidinium, or benzoimidazolium; for example, L is a $(C_2-C_6)$alkylene chain such as ethylene, propylene, or butylene;

with the proviso that, when n is 2, then m is 0, and when n is 1, then m is 1.

Another aspect of the present disclosure is a dye composition for dyeing keratin materials, for example, keratin fibers such as the hair, comprising, in a cosmetically acceptable medium, at least one indole-derived styryl dye comprising an alkyl or alkylene linker of formula (I) as disclosed herein.

Another aspect of the present disclosure is novel indole-derived styryl dyes comprising an alkyl or alkylene linker of formula (I) as disclosed herein.

The dyeing process according to the present disclosure can make it possible to visibly color dark keratin materials, such as dark hair. This process also makes it possible to dye bleached keratin fibers in a strong, relatively nonselective, homogeneous, and chromatic manner. Furthermore, the process of the present disclosure makes it possible to obtain a coloring of keratin materials without damaging said material, which is persistent with respect to shampooing operations, common attacks (sunlight, perspiration) and other hair treatments. These dyes moreover can extend the color range to yellows and reds. The process of the present disclosure also makes it possible to obtain lightening of dark keratin materials.

As used herein, "dark keratin material" means keratin material that exhibits a lightness L* measured in the C.I.E. L*a*b* system of less than or equal to 45, for instance, less than or equal to 40, given that L*=0 is equivalent to black and L*=100 is equivalent to white.

As used herein, "naturally or artificially dark hair" means hair whose tone height is less than or equal to 6 (dark blond), for example, less than or equal to 4 (chestnut-brown).

The lightening of the hair is evaluated by the variation in "tone height" before and after application of the compound of formula (I). The notion of "tone" is based on the classification of the natural shades, one tone separating each shade from the shade immediately following or preceding it. This definition and the classification of the natural shades are well known to hair styling professionals and are published in the book "Science des traitements capillaires" [*Hair Treatment Sciences*], by Charles Zviak 1988, published by Masson, pp. 215 and 278.

The tone heights range from 1 (black) to 10 (very light blond), one unit corresponding to one tone; the higher the figure, the lighter the shade.

An artificially colored hair is a hair whose color has been modified by a dyeing treatment, for example dyeing with direct dyes or oxidation dyes.

As used herein, "bleached hair" means hair whose tone height is greater than 6, for instance, greater than 7.

The composition disclosed herein should, after application to hair, for example chestnut-brown hair, lead to at least one of the results below.

Interest is focused on the hair reflectance performance levels when said hair is irradiated with visible light in the wavelength range from 400 to 700 nanometers.

The curves of reflectance as a function of wavelength, of the hair treated with the composition of the present disclosure and of untreated hair, are then compared.

The curve corresponding to the treated hair should show a reflectance in the wavelength range of from 500 to 700 nanometers which is higher than the curve corresponding to the untreated hair.

This means that, in the wavelength range of from 540 to 700 nanometers, there is at least one range where the reflectance curve corresponding to the treated hair is higher than the reflectance curve corresponding to the untreated hair. As used herein, "higher" means a difference of at least 0.05% in reflectance, and for instance, at least 0.1%. All the same, there may be, in the wavelength range of from 540 to 700 nanometers, at least one range where the reflectance curve corresponding to the treated hair is superimposable on or lower than the reflectance curve corresponding to the untreated hair.

For example, the wavelength where the difference is at a maximum between the reflectance curve of the treated hair and that of the untreated hair is within the wavelength range of from 500 to 650 nanometers, for instance, within the wavelength range of from 550 to 620 nanometers.

For the purpose of the present disclosure, and unless otherwise indicated, the "aryl" or "heteroaryl" or "benzo" radicals, or the aryl or heteroaryl part of a radical, may be substituted with at least one substituent, chosen from:

a $C_1-C_{16}$, such as $C_1-C_8$, alkyl radical optionally substituted with one or more radicals chosen from the radicals: hydroxyl, $C_1-C_2$ alkoxy, $C_2-C_4$(poly)hydroxyalkoxy, acylamino, and amino substituted with two $C_1-C_4$ alkyl radicals, which may be identical or different, optionally bearing at least one hydroxyl group, or the two radicals possibly forming, with the nitrogen atom to which they are attached, a heterocycle comprising from 5 to 7 members, such as 5 or 6 members, which is saturated or unsaturated, which is optionally substituted, and which optionally comprises another heteroatom which may be identical or different from the nitrogen;

a halogen atom such as chlorine, fluorine, or bromine;

a hydroxyl group;

$C_1-C_2$ alkoxy radical;

$C_1-C_2$ alkylthio radical;

a $C_2-C_4$ (poly)hydroxyalkoxy radical;

an amino radical;

a 5- or 6-membered heterocycloalkyl radical;

an optionally cationic 5- or 6-membered heteroaryl radical, such as imidazolium, optionally substituted with a $C_1-C_4$ alkyl radical, for example, methyl;

an amino radical substituted with one or two $C_1-C_6$ alkyl radicals, which may be identical or different, optionally bearing at least:

i) one hydroxyl group, and/or ii) one amino group optionally substituted with one or two optionally substituted $C_1-C_3$ alkyl radicals, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen;

—N(R)—C(O)—R' wherein the R radical is a hydrogen atom or a $C_1$-$C_4$ alkyl radical optionally bearing at least one hydroxyl group, and the R' radical is a $C_1$-$C_2$ alkyl radical;

$R_2N$—C(O)— wherein the R radicals, which may or may not be identical, are chosen from a hydrogen atom and a $C_1$-$C_4$ alkyl radical optionally bearing at least one hydroxyl group;

R'S(O)$_2$—N(R)— wherein the R radical is chosen from a hydrogen atom and a $C_1$-$C_4$ alkyl radical optionally bearing at least one hydroxyl group, and the R' radical is chosen from a $C_1$-$C_4$ alkyl radical and a phenyl radical;

$R_2N$—S(O)$_2$— wherein the R radicals, which may or may not be identical, are chosen from a hydrogen atom and a $C_1$-$C_4$ alkyl radical optionally bearing at least one hydroxyl group, a carboxylic radical in acid or salified form (for instance, with an alkali metal or an ammonium, which is substituted or unsubstituted);

a cyano group; and a polyhaloalkyl group comprising from 1 to 6 carbon atoms and from 1 to 6 halogen atoms, which may be identical or different; the polyhaloalkyl group is, for example, trifluoromethyl.

For the purpose of the present disclosure, and unless otherwise indicated, the heterocyclic part of a nonaromatic radical may be substituted with at least one substituent, chosen from the groups:

hydroxyl;

$C_1$-$C_4$ alkoxy;

$C_1$-$C_4$ alkyl;

$C_2$-$C_4$ (poly)hydroxyalkoxy;

a $C_1$-$C_2$ alkylthio radical;

RC(O)—N(R')— wherein the R' radical is chosen from a hydrogen atom and a $C_1$-$C_4$ alkyl radical optionally bearing at least one hydroxyl group, and the R radical is chosen from a $C_1$-$C_2$ alkyl radical and an amino radical substituted with two $C_1$-$C_4$ alkyl groups, which may be identical or different, optionally bearing at least one hydroxyl group;

RC(O)—O— wherein the R radical is chosen from a $C_1$-$C_4$ alkyl radical and an amino radical substituted with one or two $C_1$-$C_4$ alkyl groups, which may be identical or different, optionally bearing at least one hydroxyl group, said alkyl radicals may form, with the nitrogen atom to which they are attached, a heterocycle comprising from 5 to 7 members, which is saturated or unsaturated, which is optionally substituted, and which optionally comprises at least one other heteroatom which may or may not be different from nitrogen; and RO—C(O)— wherein the R radical is a $C_1$-$C_4$ alkyl radical optionally bearing at least one hydroxyl group.

For the purpose of the present disclosure, and unless otherwise indicated, a heterocyclic radical or a nonaromatic part of an aryl or heteroaryl radical may also be substituted with one or more oxo or thioxo groups.

For the purpose of the present disclosure, and unless otherwise indicated, an "aryl" radical comprises a condensed or noncondensed, monocyclic or polycyclic group comprising from 6 to 22 carbon atoms, and at least one ring of which is aromatic; for example, the aryl radical is a phenyl, biphenyl, naphthyl, indenyl, anthracenyl or tetrahydronaphthyl.

For the purpose of the present disclosure, and unless otherwise indicated, a "heteroaryl radical" comprises an optionally cationic, condensed or noncondensed, monocyclic or polycyclic group comprising from 5 to 22 members and from 1 to 6 heteroatoms chosen from a nitrogen, oxygen, sulfur, and selenium atom, and at least one ring of which is aromatic, for example, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl, and its ammonium salt.

For the purpose of the present disclosure, and unless otherwise indicated, a "heterocyclic radical or heterocycle" comprises a condensed or noncondensed, monocyclic or polycyclic, nonaromatic radical comprising from 5 to 22 members, comprising from 1 to 6 heteroatoms chosen from nitrogen, oxygen, sulfur, and selenium, such as pyrrolidine, morpholinyl, piperidinyl, or piperazinyl.

For the purpose of the present disclosure, and unless otherwise indicated, an "alkyl radical" is a linear or branched, $C_1$-$C_{16}$ hydrocarbon-based radical, such as a $C_1$-$C_8$ hydrocarbon-based radical.

For the purpose of the present disclosure, and unless otherwise indicated, "optionally substituted" assigned to the alkyl radical means that said alkyl radical may be substituted with one or more radicals chosen from the radicals: i) hydroxyl; ii) $C_1$-$C_4$ alkoxy; iii) acylamino; iv) amino optionally substituted with one or two $C_1$-$C_4$ alkyl radicals, which may be identical or different, said alkyl radicals may form, with the nitrogen atom which bears them, a heterocycle comprising from 5 to 7 members, optionally comprising another heteroatom which may or may not be different from nitrogen; v) or a quaternary ammonium group —N$^+$R'R''R''', M$^-$, wherein R', R'', and R''', which may be identical or different, are chosen from a hydrogen atom and a $C_1$-$C_4$ alkyl group, or —N$^+$R'R''R''' forms a heteroaryl such as imidazolium optionally substituted with a $C_1$-$C_4$ alkyl group, and M$^-$ represents the counterion of the corresponding organic acid, mineral acid, or halide; and vi) (di)($C_1$-$C_6$)(alkyl)aminocarbonyl group.

For the purpose of the present disclosure, and unless otherwise indicated, an "alkoxy radical" is an alkyloxy or alkyl-O-radical wherein the alkyl radical is a linear or branched $C_1$-$C_{16}$ hydrocarbon-based radical, such as a $C_1$-$C_8$ hydrocarbon-based radical.

For the purpose of the present disclosure, and unless otherwise indicated, an "alkylthio radical" is an alkyl-S— radical wherein the alkyl radical is a linear or branched $C_1$-$C_{16}$ hydrocarbon-based radical, such as a $C_1$-$C_8$ hydrocarbon-based radical.

For the purpose of the present disclosure, and unless otherwise indicated, an "alkylene chain" comprises a divalent chain; for example $C_1$-$C_6$, such as $C_1$-$C_3$, when the chain is linear; optionally substituted with at least one, identical or different, halogen atom or group chosen from hydroxyl, alkoxy, (di)(alkyl)amino, and $R^a$-$Z^a$-C($Z^b$)-, wherein $Z^a$ and $Z^b$, which may be identical or different, are chosen from an oxygen atom, a sulfur atom, and a group NR$^{a'}$; and R$^a$ is chosen from an alkali metal, a hydrogen atom, and an alkyl group; and R$^{a'}$ is chosen from a hydrogen atom and an alkyl group.

For the purpose of the present disclosure, and unless otherwise indicated, an "alkenylene chain" comprises a divalent chain; for instance, $C_2$-$C_6$, such as —C≡C—, comprising from 1 to 3 π double bonds, which may or may not be conjugated, optionally substituted with the same groups as for the alkylene chain.

For the purpose of the present disclosure, and unless otherwise indicated, a "saturated or unsaturated, optionally substituted $C_1$-$C_{20}$ hydrocarbon-based chain" comprises a hydrocarbon-based, such as $C_1$-$C_8$, chain optionally comprising from 1 to 3 π double bonds, which may or may not be conjugated, the hydrocarbon-based chain being, for instance, saturated; said chain is optionally substituted with at least one, identical or different, halogen atom or group chosen from hydroxyl, alkoxy, (di)(alkyl)amino, and $R^b$-$Z^b$-C($Z^c$), wherein $Z^b$ and $Z^c$, which may be identical or different, are chosen from an oxygen atom, a sulfur atom, and a group $NR^{b'}$; and $R^b$ is chosen from an alkali metal, a hydrogen atom, and an alkyl group; and $R^{b'}$ is a hydrogen atom or an alkyl group.

For the purpose of the present disclosure, and unless otherwise indicated, an "organic or mineral acid salt" is, for instance, chosen from a salt derived: i) from hydrochloric acid HCl; ii) from hydrobromic acid HBr; iii) from sulfuric acid $H_2SO_4$; iv) from alkylsulfonic acids: Alk-S(O)$_2$OH such as methylsulfonic acid and ethylsulfonic acid; v) from arylsulfonic acids: Ar—S(O)$_2$OH such as from benzenesulfonic acid and from toluenesulfonic acid; vi) from citric acid; vii) from succinic acid; viii) from tartaric acid; ix) from lactic acid; x) from alkoxysulfinic acids: Alk-O—S(O)OH such as from methoxysulfinic acid and from ethoxysulfinic acid; xi) from aryloxysulfinic acids such as from tolueneoxysulfinic acid and from phenoxysulfinic acid; xii) from phosphoric acid $H_3PO_4$; xiii) from acetic acid $CH_3C(O)OH$; xiv) from triflic acid $CF_3SO_3H$; and xv) from tetrafluoroboric acid $HBF_4$.

For the purpose of the present disclosure, and unless otherwise indicated, an "anionic counterion" comprises an anion or an anionic group associated with the cationic charge of the dye; for example, the anionic counterion is chosen from: i) halides such as chloride or bromide; ii) nitrates; iii) sulfonates, among which are $C_1$-$C_6$ alkyl sulfonates: Alk-S(O)$_2$O$^-$ such as methyl sulfonate or mesylate and ethyl sulfonate; iv) aryl sulfonates: Ar—S(O)$_2$O$^-$ such as benzene sulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) arylsulfates: Ar—O—S(O)O$^-$ such as benzenesulfate and toluenesulfate; xi) alkoxysulfates: Alk-O—S(O)$_2$O$^-$ such as methoxy sulfate and ethoxy sulfate; xii) aryloxysulfates: Ar—O—S(O)$_2$O$^-$; xiii) phosphate; xiv) acetate; xv) triflate; and xvi) borates such as tetrafluoroborate.

For the purpose of the present disclosure, and unless otherwise indicated, the "solvates" comprise the hydrates and also the association with linear or branched $C_1$-$C_4$ alcohols such as ethanol, isopropanol, or n-propanol.

The indole-derived styryl dyes comprising an alkyl or alkylene linker of formula (I) as disclosed herein are dyes capable of fluorescing, i.e., capable of absorbing in the UV radiation or visible range at a wavelength $\gamma_{abs}$ ranging from 250 to 800 nm and capable of re-emitting in the visible range at an emission wavelength $\gamma_{em}$ ranging from 400 to 800 nm.

As a non-limiting example, the fluorescent compounds of formula (I) of the present disclosure are dyes capable of absorbing in the visible range $\gamma_{abs}$ ranging from 400 to 800 nm and of re-emitting in the visible range $\gamma_{em}$ ranging from 400 to 800 nm. Further as a non-limiting example, the dyes of formula (I) are dyes capable of absorbing at a $\gamma_{abs}$ ranging from 400 to 550 nm and of re-emitting in the visible range at a $\gamma_{em}$ ranging from 450 to 600 nm.

One embodiment relates to the fluorescent dyes of formula (I) with n and m equal to 1.

According to another embodiment of the present disclosure, the fluorescent dyes of formula (I) are fluorescent dyes with n=2 and m=0.

Another embodiment of the present disclosure relates to the fluorescent dyes of formula (I) comprising a unit A wherein:
  a) $Z_1$ is a quaternized nitrogen atom $N^+$, and $Z_2$, $Z_3$, and $Z_4$ are $CR^4$, wherein $R^4$ is chosen from, for example, a hydrogen atom and a ($C_1$-$C_4$)alkyl group, or $Z_3$ and $Z_4$ are CH and $Z_2$ is chosen from a ($C_1$-$C_6$)alkylcarbonylamino and a (di) ($C_1$-$C_4$)(alkyl)aminocarbonyl group;
  b) $Z_2$ is a group $N^+R^5$, $Z_1$ is a carbon atom, and $Z_3$ and $Z_4$ are $CR^4$, wherein $R^4$ is, for example, a hydrogen atom;
  c) $Z_4$ is a group $N^+R^5$, $Z_1$ is a carbon atom, and $Z_3$ and $Z_2$ are $CR^4$, wherein $R^4$ is, for example, a hydrogen atom; or
  d) $Z_1$ is a quaternized nitrogen atom $N^+$, $Z_2$ and $Z_4$ are $CR^4$, and $Z_3$ is a nitrogen atom.

One embodiment of the present disclosure relates to indole-derived styryl dyes comprising an alkyl or alkylene linker of formula (Ia) below:

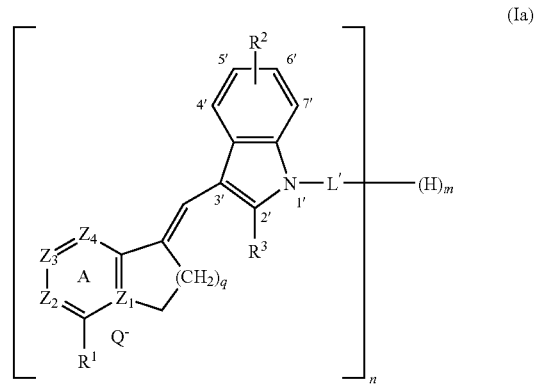

wherein:
  n, m, and $Q^-$ are as defined above;
  wherein unit A:
    a) $Z_1$ is a quaternized nitrogen atom $N^+$, and $Z_2$, $Z_3$, and $Z_4$ are $CR^4$, wherein $R^4$ is chosen from a hydrogen atom and a ($C_1$-$C_4$)alkyl group, or $Z_3$ and $Z_4$ are CH and $Z_2$ is chosen from a ($C_1$-$C_6$)alkylcarbonylamino and a (di)($C_1$-$C_4$)(alkyl)aminocarbonyl group;
    b) $Z_2$ is a group $N^+R^5$, $Z_1$ is a carbon atom, and $Z_3$ and $Z_4$ are $CR^4$, wherein $R^4$ is, for example, a hydrogen atom; and
    c) $Z_4$ is a group $N^+R^5$, $Z_1$ is a carbon atom, and $Z_3$ and $Z_2$ are $CR^4$, wherein $R^4$ is, for example, a hydrogen atom; or
    d) $Z_1$ is a quaternized nitrogen atom $N^+$, $Z_2$ and $Z_4$ are $CR^4$, and $Z_3$ is a nitrogen atom;
  q is an integer ranging from 1 to 2, such as 1;
  $R^1$ is chosen from a hydrogen atom and a ($C_1$-$C_6$)alkyl group; for example, $R^1$ is a hydrogen atom;
  $R^2$ is absent, or is chosen from a halogen atom such as chlorine, a ($C_1$-$C_3$)alkoxy, and a ($C_1$-$C_3$)alkoxycarbonyl group; for example, at position 5' or 6';
  $R^3$ is chosen from a hydrogen atom, a ($C_1$-$C_6$)alkyl group such as methyl, a phenyl group, a (di)($C_1$-$C_6$)(alkyl) amino group such as dimethylamino, and a monocyclic, 5- to 7-membered heterocycloalkyl group comprising from 1 to 3 heteroatoms chosen from oxygen and nitrogen, optionally substituted with a (C$_1$-C$_2$)alkyl group such as piperazino;

R$^5$ is chosen from an optionally substituted (C$_1$-C$_6$)alkyl group, and an aryl(C$_1$-C$_6$)alkyl; for instance, R$^5$ is a (C$_1$-C$_4$)alkyl group such as methyl or ethyl;

L' is chosen from a as bond, a (C$_2$-C$_6$)alkylene chain such as ethylene —(CH$_2$)$_2$—, propylene —(CH$_2$)$_3$—, or butylene —(CH$_2$)$_4$—, for example, ethylene; and a (C$_1$-C$_6$)alkyl group optionally substituted with, for instance, a (di)(C$_1$-C$_6$)(alkyl)aminocarbonyl group;

with the proviso that when n is 2, then m is 0, and when n is 1, then m is 1.

By way of example, non-limiting mention may be made of the following fluorescent dyes of formula (I) or (Ia)

1
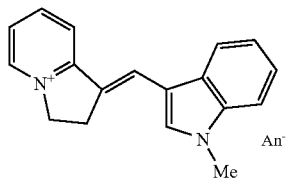

2
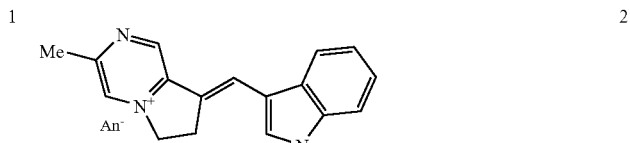

3
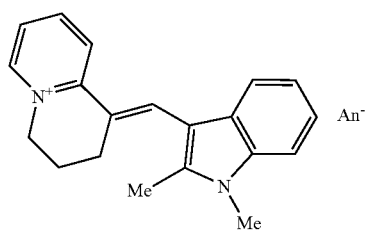

4
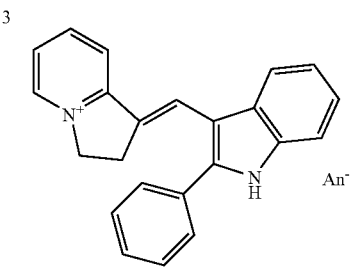

5
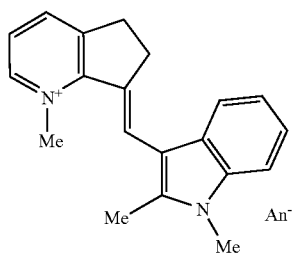

6
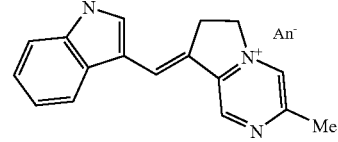

7
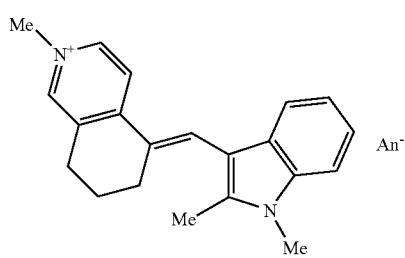

8
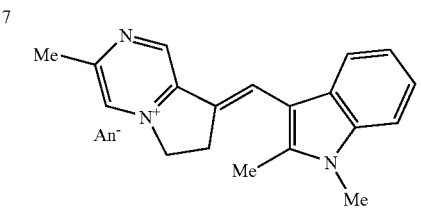

-continued
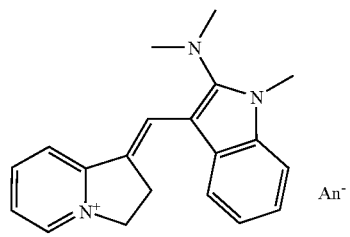
9
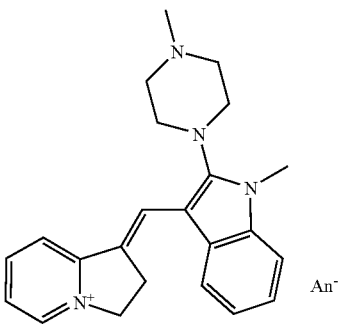
10
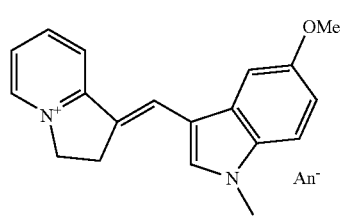
11
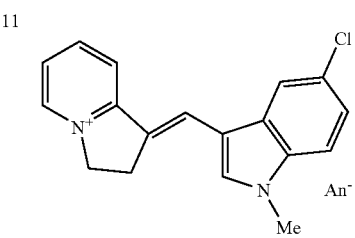
12
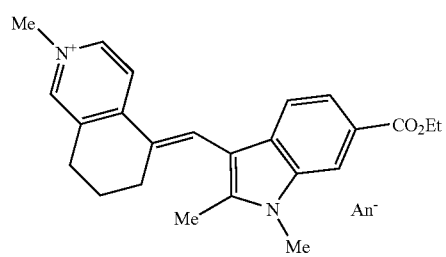
13
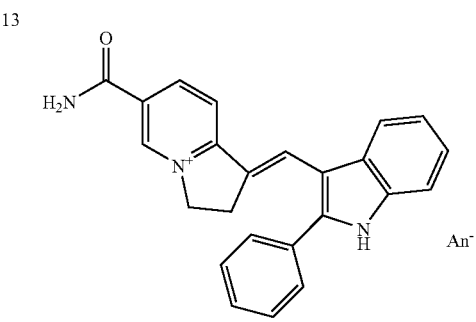
14
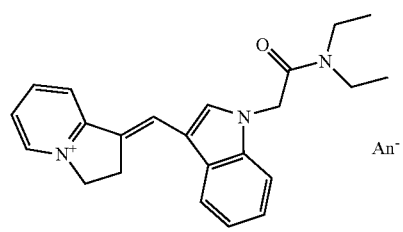
15
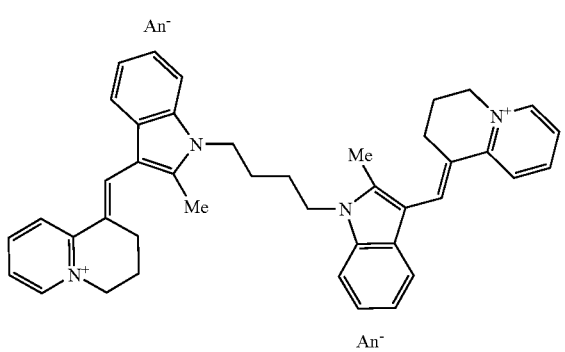
16
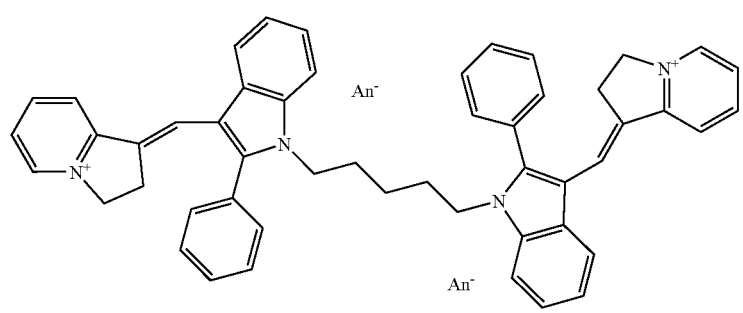
17

-continued
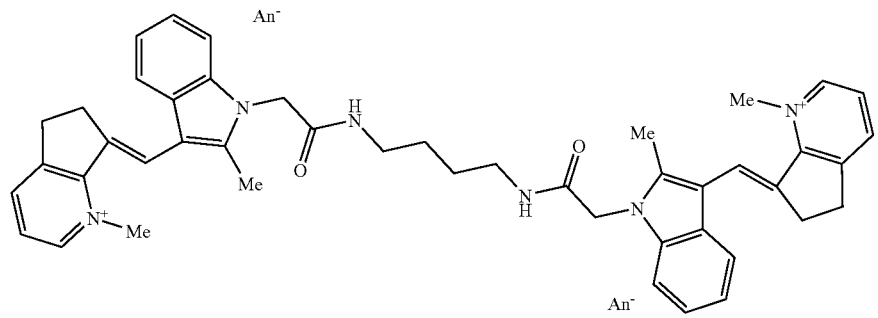
18
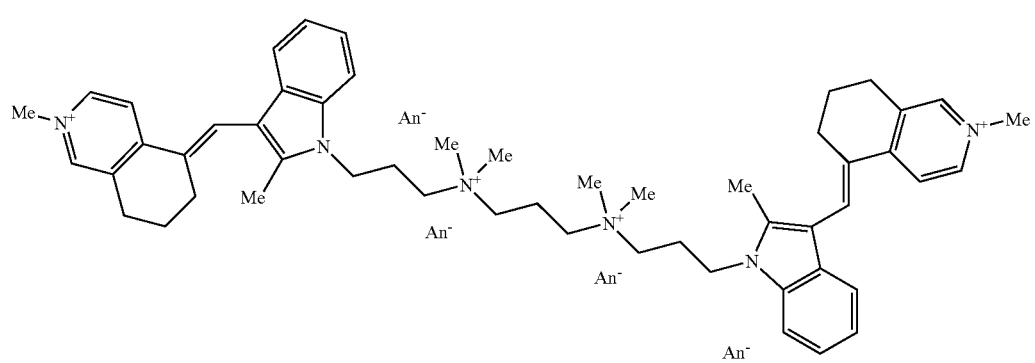
19
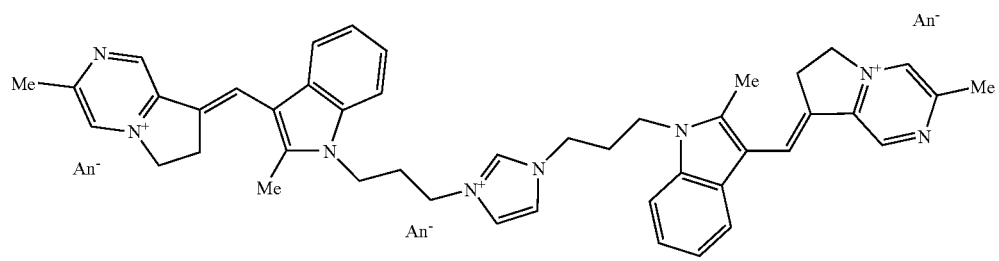
20
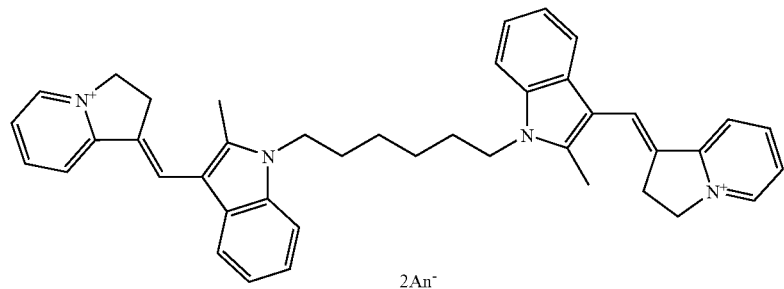
21
wherein An⁻ is an anionic counterion.

For all the exemplary embodiments which follow, of preparation of the novel indole-derived styryl dyes comprising an alkyl or alkylene linker of formula (I), those skilled in the art know how to pre-protect the reactive functions and then to deprotect them for the needs of the synthesis reaction, by the known conventional methods of protection/deprotection such as those described in the books mentioned above by T. W Greene John Willey & Sons ed., NY, 1981, or P. Kocienski "*Protecting Groups*", P. Kocienski, Thieme, 3rd ed., 2005.

The fluorescent dyes of formula (I) can be synthesized in a single stage by reaction of an indole-3-carboxaldehyde compound (a) with a cationic heteroaromatic compound (b) so as to give, by Knoevenagel condensation, the styryl fluorescent dyes (I).

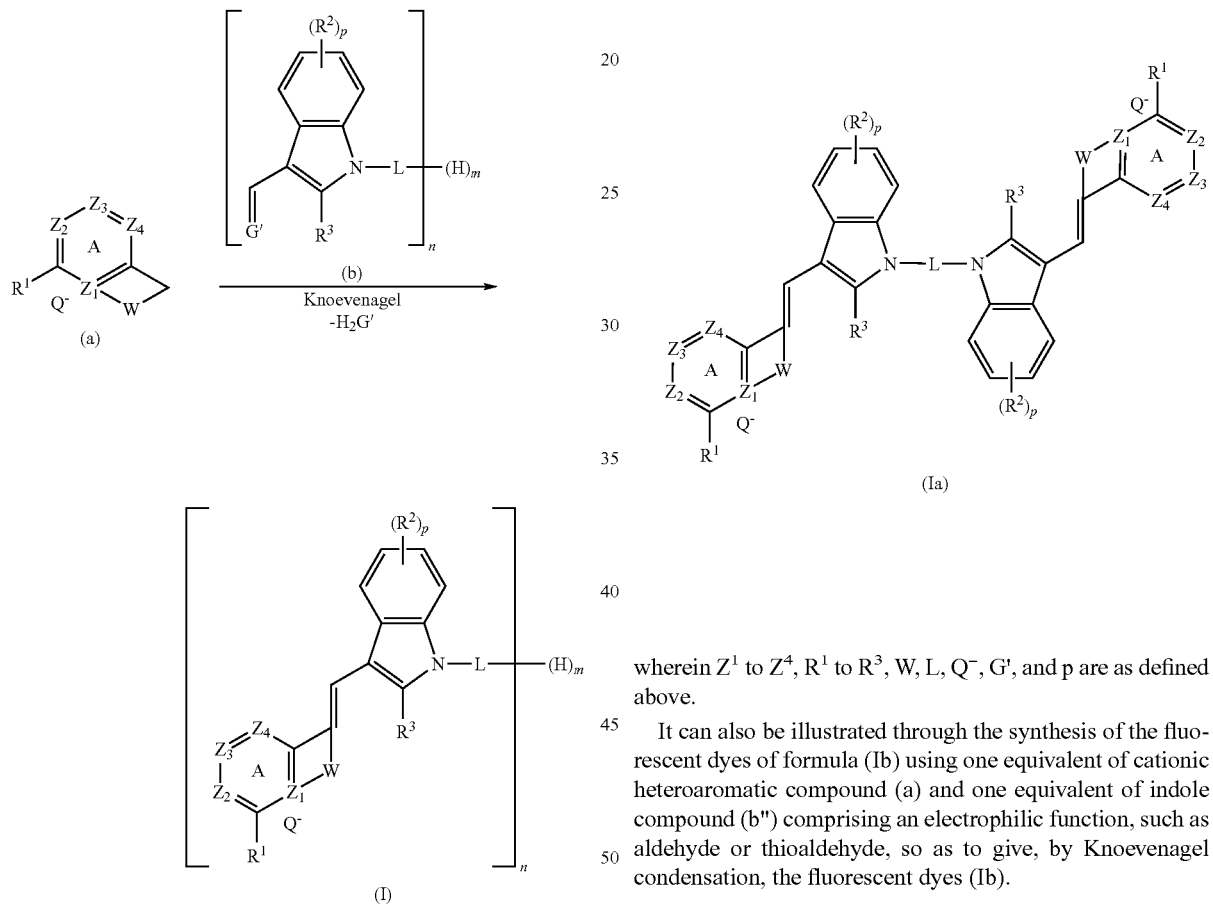

wherein $Z^1$ to $Z^4$, $R^1$ to $R^3$, W, L, $Q^-$, m, n, and p are as defined above; G' is chosen from an oxygen atom, a sulfur atom, and a group NR', wherein R' is chosen from a hydrogen atom and an alkyl radical, and R is chosen from a hydrogen atom, a $C_1$-$C_4$ alkyl, a $C_1$-$C_4$ hydroxyalkyl radical, and an aryl($C_1$-$C_4$)alkyl.

It is possible to illustrate this method through the synthesis of the fluorescent dyes of formula (I') using 2 equivalents of cationic heteroaromatic compound (a) and one equivalent of indole compound (b') comprising two electrophilic functions, such as aldehyde or thioaldehyde, so as to give, by double Knoevenagel condensation, the fluorescent dyes (Ia).

wherein $Z^1$ to $Z^4$, $R^1$ to $R^3$, W, L, $Q^-$, G', and p are as defined above.

It can also be illustrated through the synthesis of the fluorescent dyes of formula (Ib) using one equivalent of cationic heteroaromatic compound (a) and one equivalent of indole compound (b'') comprising an electrophilic function, such as aldehyde or thioaldehyde, so as to give, by Knoevenagel condensation, the fluorescent dyes (Ib).

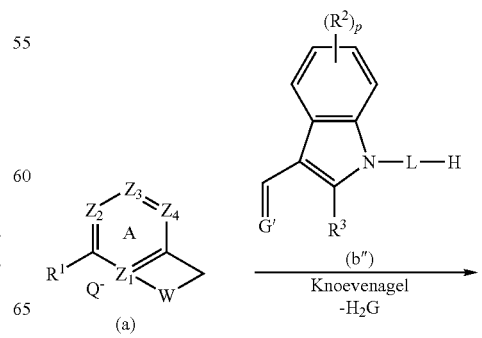

-continued

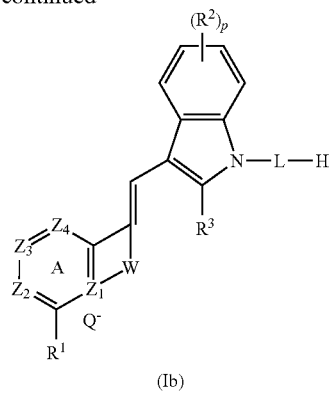

(Ib)

wherein $Z^1$ to $Z^4$, $R^1$ to $R^3$, W, L, $Q^-$, G', and p are as defined above.

Reference may be made to the book *Advanced Organic Chemistry*, "Reactions, Mechanisms and Structures", J. March, 4th ed., John Willey & Sons, 1992, for further details on the operating conditions used for the process mentioned above.

The starting reactants are commercially available or accessible by conventional methods known to those skilled in the art.

By way of example of the commercially available heteroaromatic compounds, non-limiting mention may be made of 5,6,7,8-tetrahydroisoquinoline (CAS No. 36556-06-6), 5,6,7,8-tetrahydroquinoline (CAS No. 10500-57-9), and 6,7-dihydro-5H-cyclopenta[b]pyridine (CAS No. 533-37-9).

These commercially available heteroaromatic compounds may be quaternized by the conventional methods known to those skilled in the art, so as to form the cationic heteroaromatic compounds (b).

By way of example, for the pathways for synthesizing the cationic heteroaromatic compounds (b), non-limiting mention may be made of *J.O.C.*, 68(26), 10123-10129, 2003, and *Tetrahedron Letters*, 31(24), 3495-6, 1990, for the synthesis of the 2,3-dihydro-1H-indolizinium compounds; *J.O.C.* 70(21), 8508-12, 2005; *Heterocycles* 66, 161-166, 2005, for the synthesis of the 1,2,3,4-tetrahydroquinolizinium compounds; *Tetrahedron* 46(7), 2561-72, 1990, and *J.O.C.* 51(6), 872-5, 1986, for the synthesis of the 5,6,7,8-tetrahydroquinolinium compounds and *Faming Zhuanli Shenquing Gongkai Shuomingshu* 1907973, 07 Feb. 2007, and *J.O.C.* 68(18) 6959-6966, 2003, for the synthesis of the 6,7-dihydro-5H-cyclopenta[b]pyridinium compounds.

By way of example of the commercially available indole-3-carboxaldehyde compounds (b), non-limiting mention may be made of indole-3-carboxaldehyde (CAS No. 487-89-8), 5-methoxyindole-3-carboxaldehyde (CAS No. 10601-19-1), 2-methylindole-3-carboxaldehyde (CAS No. 5416-80-8), 1-methylindole-3-carboxaldehyde (CAS No. 19012-03-4), 1-methyl-2-phenyl-3-formylindole (CAS No. 1757-72-8), and methyl 3-formylindole-6-carboxylate (CAS No. 133831-28-4).

By way of example of the commercially available indole-3-carboxaldehyde compounds (b'), non-limiting mention may be made of 1,1-(2-hydroxy-1,3-propyldiyl)bis(1H-indole-3-carboxaldehyde) (CAS No. 331275-74-2) and 1-(1,4-butanediyl)bis(1H-indole-3-carboxaldehyde) (CAS No. 676244-31-8).

By way of example for the pathways for synthesizing the indole-3-carboxaldehyde compounds (b'), non-limiting mention may be made of *Letters in Organic Chemistry*, 3(9), 712-704, 2006 and *Organic & Biomolecular Chemistry*, 2(19), 2874-2883, 2004.

According to another synthetic process, a compound (e) comprising a nucleophilic function can be reacted with a sufficient, such as equimolar, amount of a fluorescent dye (Ic) which comprises an electrophilic function, so as to form a Σ covalent bond; see below, the preparation of dyes of formula (Id):

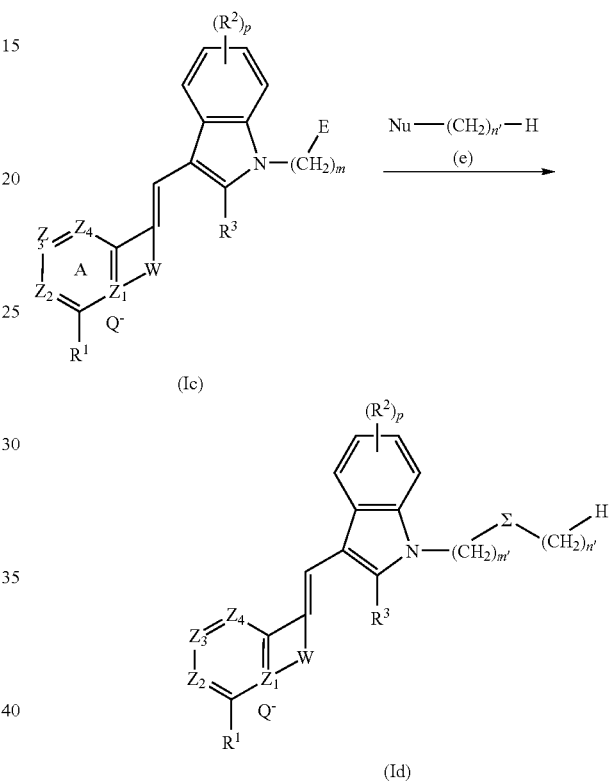

wherein $Z^1$ to $Z^4$, $R^1$ to $R^3$, W, $Q^-$, and p are as defined above; m' and n' are integers ranging from 1 to 6, wherein m'+n' is an integer ranging from 2 to 6, Nu representing a nucleophilic group; E representing an electrophilic group; and Σ representing the bond generated after attack by the nucleophile on the electrophile.

By way of non-limiting example, the Σ covalent bonds that can be generated are listed in the table below based on condensation of electrophiles with nucleophiles:

| Electrophiles E | Nucleophiles Nu | Σ Covalent bonds |
|---|---|---|
| Activated esters* | Amines | Carboxamides |
| Acyl nitrides** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |

-continued

| Electrophiles E | Nucleophiles Nu | Σ Covalent bonds |
|---|---|---|
| Sulfonic acids and salts thereof | Thiols | Thioethers |
| Sulfonic acids and salts thereof | Carboxylic acids | Esters |
| Sulfonic acids and salts thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-acylureas |
| Diazoalkanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulfonic esters | Amines | Aikylamines |
| Sulfonic esters | Thiols | Thioethers |
| Sulfonic esters | Carboxylic acids | Esters |
| Sulfonic esters | Alcohols | Ethers |
| Sulfonyl halides | Amines | Sulfonamides |

*the activated esters of general formula —CO-Part with Part representing a leaving group such as oxysuccinimidyl, oxybenzotriazolyl, aryloxy which is optionally substituted;
**the acyl nitrides may rearrange to give isocyanates.

At least one embodiment of this process is to use a styryl dye having an electrophilic acrylate function (—OCO—C=C—) on which is carried out an addition reaction that will generate a Σ bond.

One aspect of this process is to use a styryl dye (Ie) having a nucleophilic function on which is reacted a compound (f) which comprises an electrophilic function, so as to form a Σ covalent bond; see below, the preparation of dyes of formula (If):

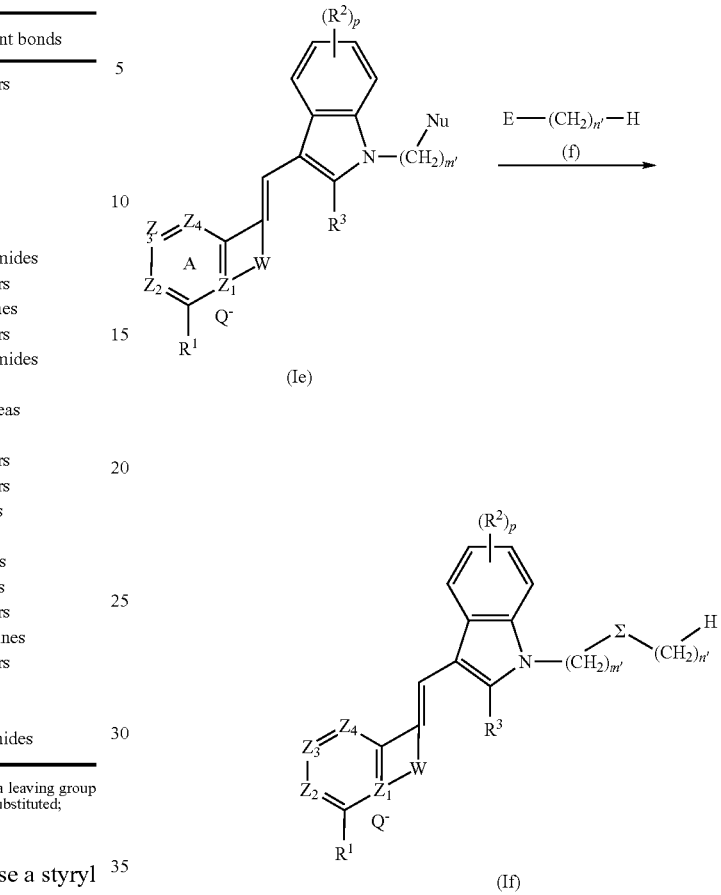

wherein $Z^1$ to $Z^4$, $R^1$ to $R^3$, W, $Q^-$, L, Nu, E, Σ, and p are as defined above.

Another aspect of this process is to react two equivalents of a styryl dye (Ie) having a nucleophilic function with one equivalent of a compound (g) which comprises two electrophilic functions, so as to form two Σ covalent bonds; see below, the preparation of dyes of formula (Ig):

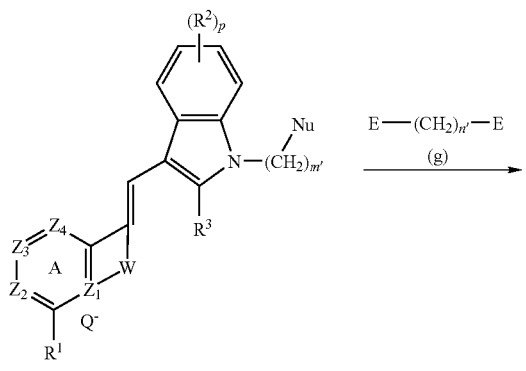

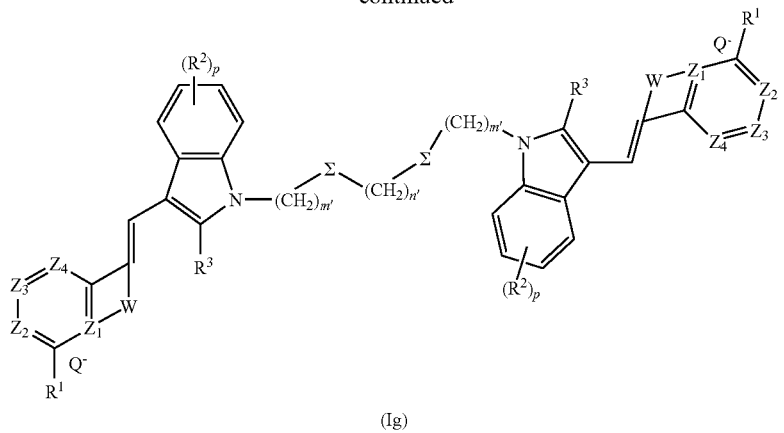

(Ig)

wherein $Z^1$ to $Z^4$, $R^1$ to $R^3$, W, $Q^-$, Nu, E, Σ, p, n', and m' are as defined above.

Another aspect of this process is to react two equivalents of a styryl dye (Ic) having an electrophilic function with one equivalent of a compound (h) which comprises two nucleophilic functions, so as to form two Σ covalent bonds; see below, the preparation of dyes of formula (Ih):

wherein $Z^1$ to $Z^4$, $R^1$ to $R^3$, W, $Q^-$, Nu, E, Σ, p, n', and m' are as defined above.

Another aspect of this process is to react a styryl dye (Ic) having an electrophilic function with a styryl dye (Ie) having a nucleophilic function, so as to form a dye (Ii) with a Σ covalent bond; see below, the preparation of dyes of formula (Ii):

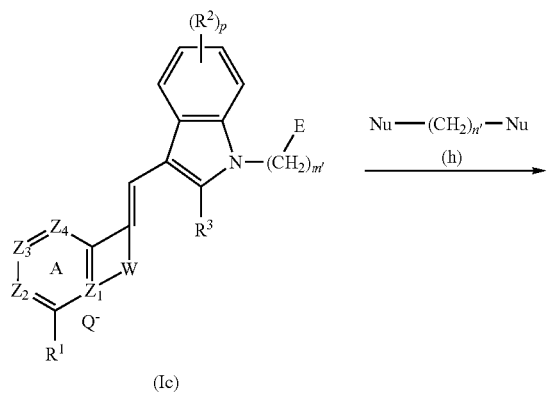

(Ic)

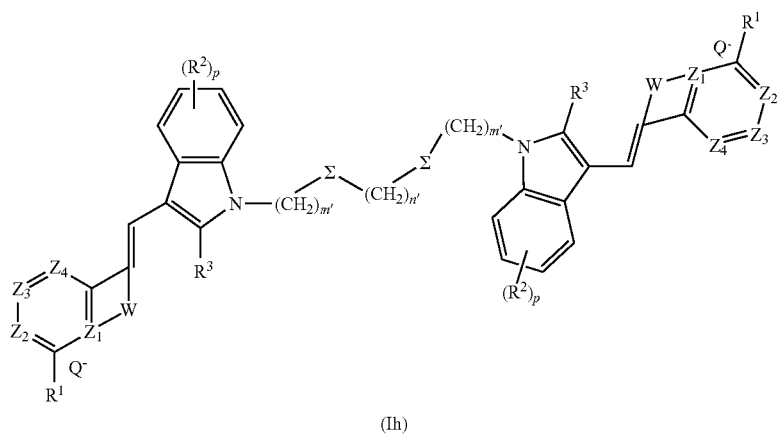

(Ih)

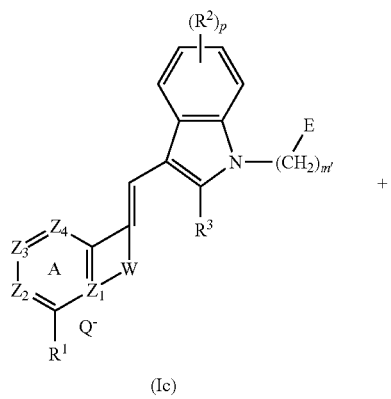

(Ic)

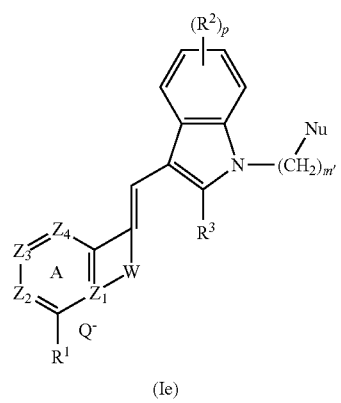

(Ie)

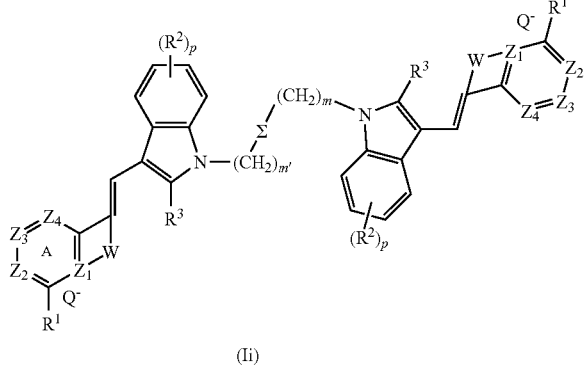

(Ii)

wherein $Z^1$ to $Z^4$, $R^1$ to $R^3$, W, $Q^-$, Nu, E, Σ, p, n', and m' are as defined above.

In accordance with another aspect of this process, the fluorescent dyes (Ij) can be obtained by reaction of a compound (j) comprising a nucleofuge leaving group Lg, for instance mesylate, tosylate, triflate, or halide, with a chromophore (Ik).

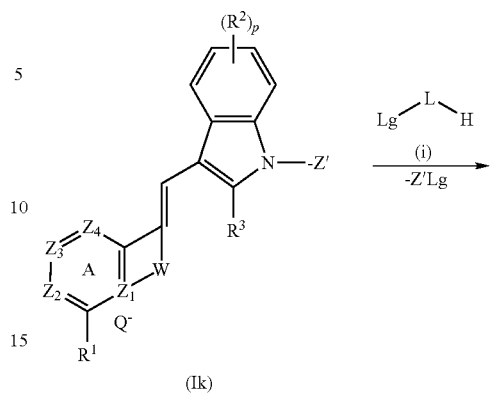

(Ik)

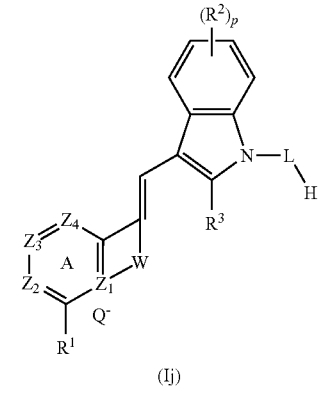

(Ij)

wherein $Z^1$ to $Z_4$, $R^1$ to $R^3$, W, $Q^-$, L, and p are as defined above, and Z' is chosen from a hydrogen atom and a group activating the nucleophilicity of the nitrogen atom of the indole moeity.

Reference may be made to the book *Advanced Organic Chemistry*, "Reactions, Mechanisms and Structures", J. March, 4th Ed., John Willey & Sons, 1992 or T. W. Greene "*Protective Groups in Organic Synthesis*", for further details on the operating conditions used for the processes mentioned above.

Another aspect of the present disclosure relates to a composition comprising at least one indole-derived styryl dye comprising an alkyl or alkylene linker of formula (I).

As a non-limiting example, the dye composition that can be used in the present disclosure comprises an amount of fluorescent dye of formula (I) ranging from 0.001% to 50% relative to the total weight of the composition. For instance, this amount may range from 0.005% to 20% by weight, such as from 0.01% and 5% by weight, relative to the total weight of the composition.

The dye composition may also comprise additional direct dyes. These direct dyes are, for example, chosen from neutral, acidic, or cationic nitrobenzene direct dyes, neutral, acidic, or cationic azo direct dyes, tetraazapentamethine dyes, neutral, acidic, or cationic quinone, such as anthraquinone dyes, azine direct dyes, triarylmethane direct dyes, indoamine direct dyes, and natural direct dyes.

Among the natural direct dyes, non-limiting mention may be made of lawsone, juglone, alizarin, purpurin, carminic acid, kermesic acid, purpurogallin, protocatechaldehyde, indigo, isatin, curcumin, spinulosin, and apigenindin. Extracts or decoctions containing these natural dyes, such as poultices or henna-based extracts, may also be used.

The dye composition may comprise at least one oxidation base and/or at least one coupler conventionally used for dyeing keratin fibers.

Among the oxidation bases, non-limiting mention may be made of para-phenylenediamines, bisphenylalkylenediamines, para-aminophenols, bis-para-aminophenols, ortho-aminophenols, heterocyclic bases, and addition salts thereof.

Among these couplers, non-limiting mention may be made of meta-phenylenediamines, meta-aminophenols, meta-diphenols, naphthalene couplers, heterocyclic couplers, and addition salts thereof.

The at least one coupler is generally present in an amount ranging from 0.001% to 10% by weight relative to the total weight of the dye composition, such as from 0.005% to 6%.

The at least one oxidation base present in the dye composition is in general present in an amount ranging from 0.001% to 10% by weight relative to the total weight of the dye composition, for example, from 0.005% to 6% by weight.

In at least one embodiment, the addition salts of the oxidation bases and of the couplers that can be used in the context of the present disclosure are chosen from addition salts with an acid, such as hydrochlorides, hydrobromides, sulfates, citrates, succinates, tartrates, lactates, tosylates, benzenesulfonates, phosphates, and acetates, and addition salts with a base, such as hydroxides of an alkali metal such as sodium or potassium, aqueous ammonia, amines, or alkanolamines.

The cosmetically acceptable medium suitable for dyeing, also called dye support, is a cosmetically acceptable medium generally constituted of water or of a mixture of water and at least one organic solvent. By way of organic solvent, non-limiting mention may, for example, be made of $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether, and diethylene glycol monomethyl ether, and also aromatic alcohols such as benzyl alcohol or phenoxyethanol, and mixtures thereof.

The solvents, when they are present, may be present, for example, in proportions ranging from 1% to 40% by weight approximately, relative to the total weight of the dye composition, and such as from 5% to 30% by weight approximately.

The dye composition may also comprise various adjuvants conventionally used in hair-dyeing compositions, such as anionic, cationic, nonionic, amphoteric, or zwitterionic surfactants or mixtures thereof, anionic, cationic, nonionic, amphoteric, or zwitterionic polymers, or blends thereof, mineral or organic thickeners, and for instance anionic, cationic, nonionic, and amphoteric associative polymer thickeners, antioxidants, penetrating agents, sequestering agents, fragrances, buffers, dispersing agents, conditioning agents such as, for example, modified or unmodified, volatile or nonvolatile silicones, such as amino silicones, film-forming agents, ceramides, preservatives, opacifiers, or conductive polymers.

The above adjuvants may be present in an amount, for each of them, ranging from 0.01% to 20% by weight relative to the weight of the composition.

Of course, those skilled in the art will take care to select this or these possible additional compounds in such a way that the advantageous properties intrinsically associated with the dye composition in accordance with the present disclosure are not, or are not substantially, impaired by the addition(s) envisaged.

The pH of the dye composition may range from 3 to 14 approximately, for instance, from 5 to 11 approximately. It may be adjusted to the desired value by means of acidifying or basifying agents normally used in the dyeing of keratin fibers or else by means of conventional buffer systems.

Among the acidifying agents, non-limiting mention may, by way of example, be made of mineral or organic acids, such as hydrochloric acid, orthophosphoric acid, sulfuric acid, carboxylic acids, for instance acetic acid, tartaric acid, citric acid or lactic acid, or sulfonic acids.

Among the basifying agents, non-limiting mention may, by way of example, be made of aqueous ammonia, alkali carbonates, alkanolamines such as mono-, di-, and triethanolamines, and also derivatives thereof, sodium hydroxide or potassium hydroxide and the compounds of formula (γ) below:

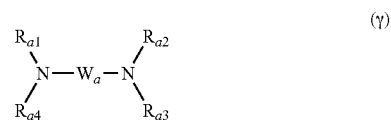

(γ)

wherein $W_a$ represents a propylene residue optionally substituted with a hydroxyl group or a $C_1$-$C_4$ alkyl radical; $R_{a1}$, $R_{a2}$, $R_{a3}$, and $R_{a4}$, which may be identical or different, are chosen from a hydrogen atom, a $C_1$-$C_4$ alkyl radical, and a $C_1$-$C_4$ hydroxyalkyl radical.

The dye composition may be in various forms, such as in the form of a liquid, a cream or a gel, or in any other form suitable for dyeing keratin fibers, such as the hair.

Another aspect of the present disclosure is a process for dyeing keratin fibers, such as dark keratin fibers, with a lightening effect, comprising applying a dye composition comprising at least one fluorescent dye of formula (I) or (Ia) as disclosed herein to said fibers.

The application of the dye composition according to the present disclosure can be carried out at ambient temperature. It may, however, be carried out at temperatures ranging from 20 to 180° C.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples which follow serve to illustrate the present disclosure without, however, being limiting in nature. The dyes of the examples hereinafter have been characterized by conventional spectroscopic and spectrometric methods.

EXAMPLES

Example 1

1-[(1-Methyl-1H-indol-3-yl)methylene]-2,3-dihydro-1H-indolizinium chloride [1]

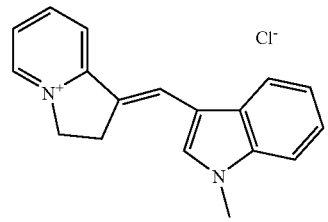

[1]

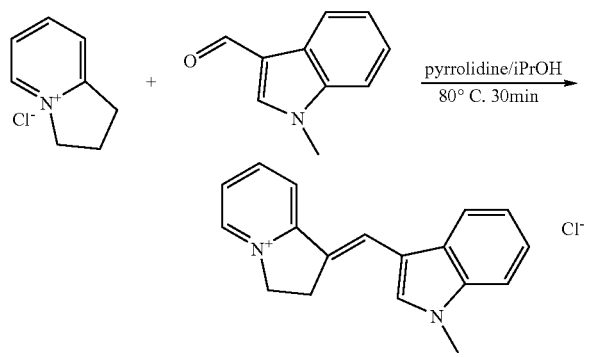

1.55 g of 2,3-dihydro-1H-indolizinium chloride and 1.59 g of 1-methylindole-3-carboxaldehyde were suspended in 15 ml of isopropanol, in a 50 ml three-necked flask. The reaction mixture was heated at 80° C. and then 820 µl of pyrrolidine were introduced. The reaction mixture was immediately cooled to ambient temperature. The precipitate was filtered off, and washed with 2 times 30 ml of isopropanol before being dried under a strong vacuum in the presence of $P_2O_5$, until a constant weight was obtained. 2.59 g of orange powder were recovered. The analyses (NMR) (d6-DMSO) and mass spectrometry ESI+M/Z=261) were in conformity with the expected structure.

Example 2

1-{[1-Methyl-2-(4-methylpiperazin-1-yl)-1H-indol-3-yl]methylene}-2,3-dihydro-1H-indolizinium acetate [2]

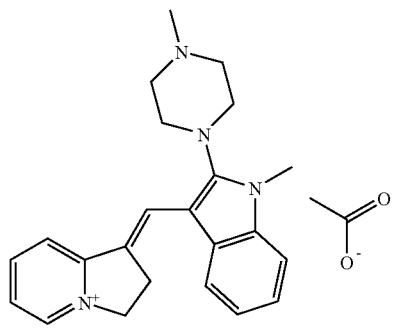

[2]

Synthesis scheme

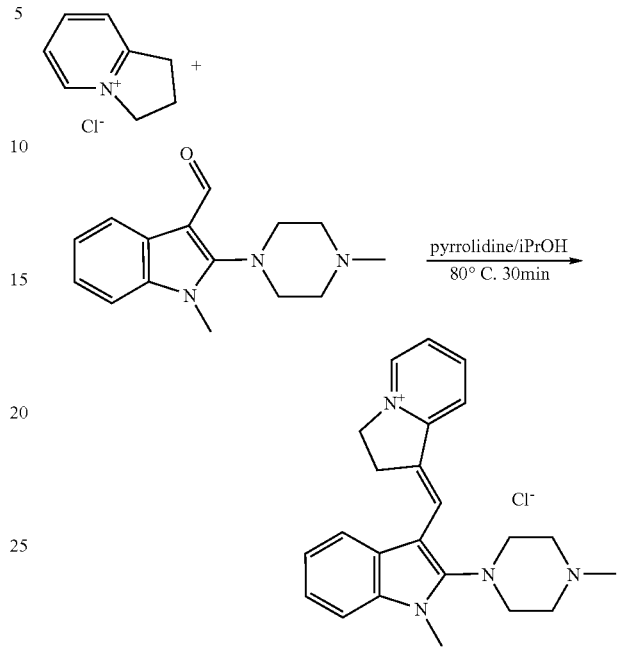

0.395 g of 1-methyl-2-(4-methylpiperazino)-1H-indole-3-carbaldehyde was solubilized in 7 ml of isopropanol. 0.138 g of piperidine was added, followed by 0.218 g of 2,3-dihydro-1H-indolizinium chloride dissolved in 7 ml of isopropanol. The reaction mixtures were brought to 80° C. for 24 h, with stirring. 50 ml of ethyl acetate were added in order to precipitate the dye. The precipitate was filtered off, and washed with 3 times 25 ml of ethyl acetate before being dried under vacuum until a constant weight was obtained. The orange powder was purified by chromatography. The analyses were in conformity with the expected structure.

Mass spectrometry: the expected cation $[C_{23}H_{27}N_4]^+$ was mainly detected. ESP+=180, 201 and 359 (corresponding to $[M+H]^{2+}$, $[M+H+CH_3CN]^{2+}$, and $[M]^+$). NMR: the spectrum was in accordance with the expected structure. HPLC: a relative UV purity of greater than 95%. Lamda max=408 nm.

Example 3

1-({1-[2-(Diethylamino)-2-oxoethyl]-1H-indol-3-yl}methylene)-2,3-dihydro-1H-indolizinium chloride [3]

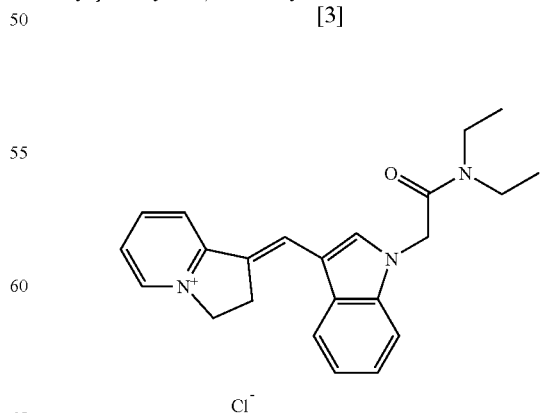

[3]

Synthesis scheme

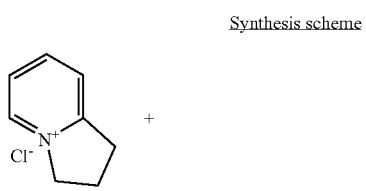

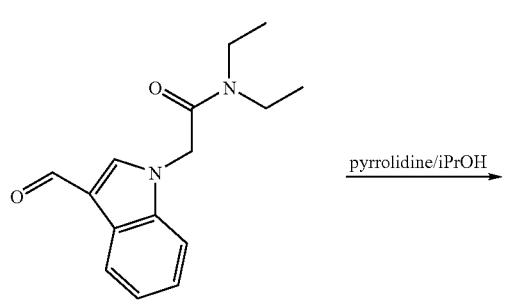

0.800 g of N,N-diethyl-2-(3-formyl-1H-indol-1-yl)acetamide was solubilized in 4.2 ml of isopropanol. 0.238 g of piperidine was added, followed by 0.435 g of 2,3-dihydro-1H-indolizinium chloride dissolved in 7 ml of isopropanol. The reaction mixtures were brought to 80° C. for 24 h, with stirring. 50 ml of ethyl acetate were added in order to precipitate the dye. The precipitate was filtered off, and washed with 3 times with 25 ml of ethyl acetate before being dried under vacuum until a constant weight was obtained. 1.09 g of orange powder were recovered. The analyses were in conformity with the expected structure.

Example 4

Synthesis of 5-[(1,2-dimethyl-1H-indol-3-yl)methylidene]-2-methyl-5,6,7,8-tetrahydroiso-quinolinium mesylate

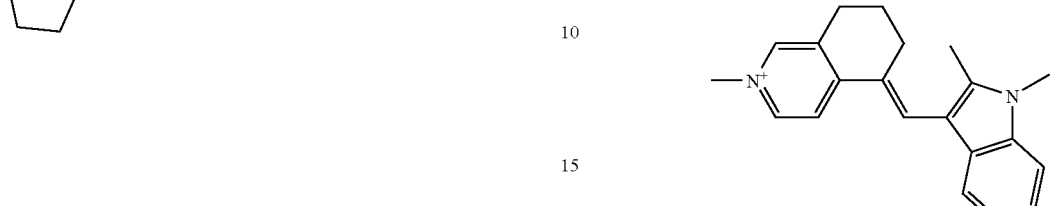

[4]

Synthesis scheme

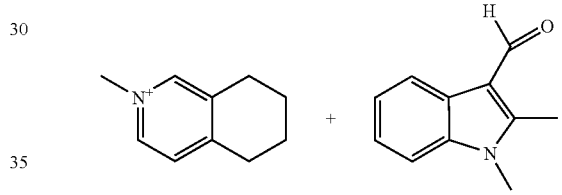

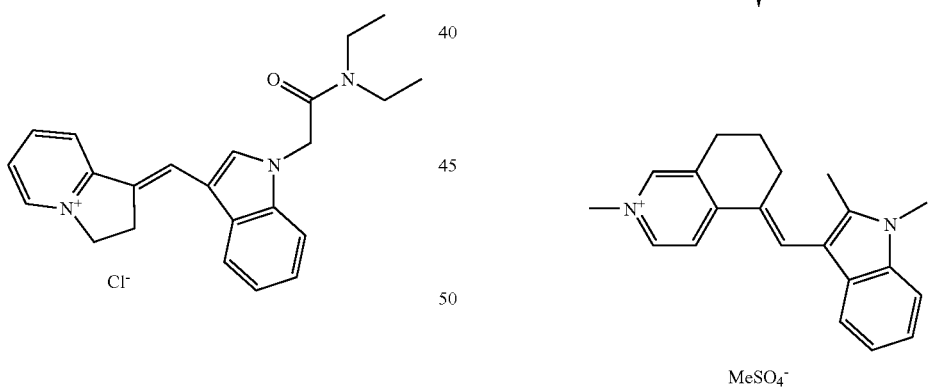

[4]

To a stirring solution of compound 2-methyl-5,6,7,8-tetrahydroisoquinolinium mesylate (0.273 g, 1 mmol) and 1,2-dimethyl-1H-indole-3-carbaldehyde (0.260 g, 1.5 mmol) in 5 ml of ethanol was added 0.1 ml of piperidine as a catalyst. The reaction mixture was heated under reflux for 20 h. After cooling, the solvent was removed under vacuum. The resulting residue was subjected to chromatography on alumina (eluent: dichloromethane/methanol=100:1 to 50:1) twice to afford 0.1 g of pure compound [4]. Analyses were in accordance with the expected structure.

Example 5
Synthesis of (1,1'-{hexane-1,6-diylbis[(2-methyl-1H-indole-1,3-diyl)methylylidene]}bis(2,3-dihydro-1H-indolizinium)dibromide [5]
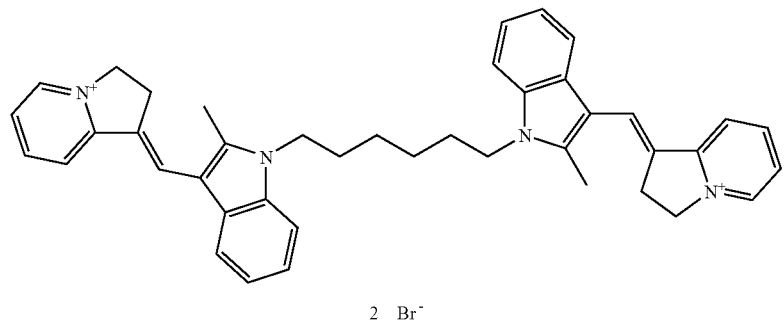
[5]
Reaction scheme
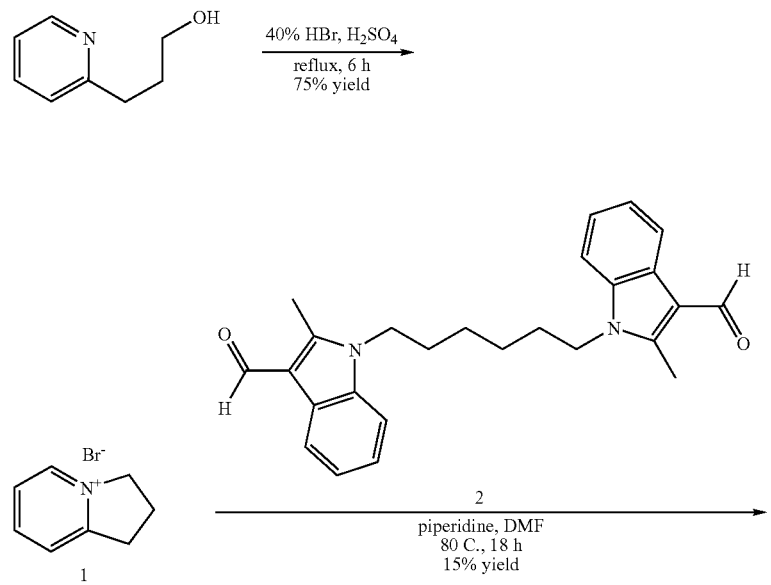
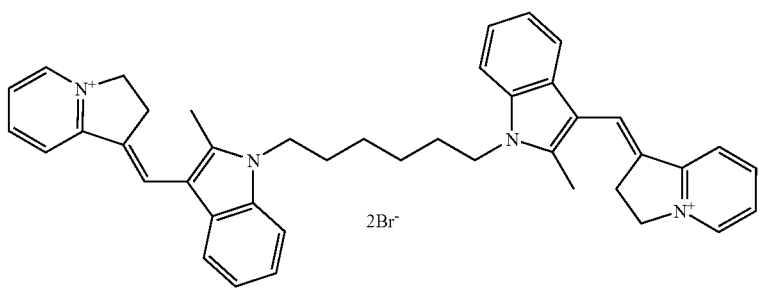
[5]

Synthesis of compound 1: A mixture of 4.1 μg (30 mmol) of 2-(3-hydroxypropyl)pyridine, 13.7 ml (120 mmol) of 48% hydrobromic acid, and 3.3 ml (60 mmol) of concentrated sulfuric acid was heated at reflux for 6 h. The water was removed and ethanol was added. Then, the resulting solids were filtered off and the filtrate was concentrated under vacuum. The residue was subjected to chromatography on silica gel (eluent: $CH_2Cl_2/MeOH=10/1$) to afford 4.5 g of desired product 1 in 75% yield.

Synthesis of compound 2: To a stirring solution of 2-methylindole-3-carboxaldehyde (6.36 g, 40 mmol) in 90 ml of THF was added portionwise 2.7 g (67.5 mmol) of NaH. After stirring for half an hour, 2.3 ml (15 mmol) of 1,6-dibromohexane was added. The mixture was allowed to stir for another 22 h at room temperature. Then the reaction was quenched by addition of some water. The organic layer was extracted with dichloromethane three times. The combined extracts were dried over anhydrous $MgSO_4$, filtered, and evaporated. The resulting residue was subjected to silica chromatography (eluent: $CH_2Cl_2/MeOH=10/1$) to afford the crude product. Further purification by recrystallization from ethanol gave 2.8 g of pure compound 2 with a 63% yield.

Synthesis of compound [5]: To a stirring solution of compound 1 (0.4 g, 2 mmol) and compound 2 (0.35 g, 0.88 mmol) in 10 ml of DMF was added 0.5 ml of piperidine as a catalyst. The reaction mixture was heated at 80 C for 18 h. After cooling, the solvent DMF was removed under vacuum. The resulting residue was subjected to chromatography on alumina (eluent: $CH_2Cl_2/MeOH=500:5$ to 500:10). The crude product was further purified by recrystallization from the mixture solvents (EtOH/EtOAc=1:3) to afford 0.1 g of desired compound [5].

Analyses were in accordance with the expected structure.

Dyeing Example

Example 1

Dyeing Process—Compound [1]

The dye composition was prepared in the following proportions.

Solution 1

| | |
|---|---|
| Hydroxyethylcellulose Natrosol 250MR | 0.72 g |
| C8/C10(50:50) alkyl hydroxyethylcellulose CG110 | 5 g |
| Benzyl alcohol | 4 g |
| Polyethylene glycol 400 | 4 g |
| Water | Qs 100 g |

Solution 2: buffer pH 7

| | |
|---|---|
| $KH_2PO_4$ | 0.026 mol/l |
| $Na_2PO_4$ | 0.041 mol/l |
| Demineralized water | qs 500 ml |

The dye composition was obtained by dissolving the dye [1] ($5 \times 10^{-3}$ mol/l) in solution 1 and then adding an equivalent volume of buffer solution 2.

The composition was applied to gray hair containing 90% white hairs (NW), bleached hair and dark hair (tone height 4, TH4). After a leave-in time of 30 min, the locks were rinsed, washed with a standard shampoo, rinsed again, and then dried.

Visual Observations

Coloring:

The lock of tone height 4 became visually lighter than untreated control locks.

The locks of gray hair containing 90% white hairs (NW) and of bleached hair were colored with strong shades:

| Compound [1] | Color obtained |
|---|---|
| Gray hair containing 90% white hairs (NW) | Bright orangey-yellow |
| Bleached hair | Bright orangey-yellow |

During the rinsing and the shampooing operations of the examples [1], there was very little visible bleeding of the color, the shampoo foams and the rinsing waters were barely colored.

The orangey-yellow color was conserved on the gray hair containing 90% white hairs and the bleached hair.

The lightening effect on the dark hair (tone height 4, TH4) remained visible.

What is claimed is:

1. A fluorescent dye of formula (I):

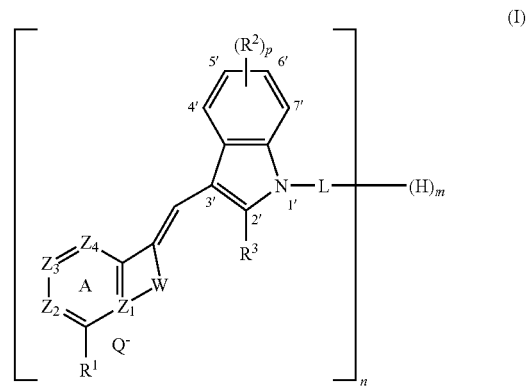

the organic or mineral acid salts thereof, optical isomers and geometric isomers thereof, or the solvates thereof:

wherein:

n is an integer ranging from 1 to 2;

m is an integer ranging from 0 to 1;

p is an integer ranging from 0 to 4;

$Q^-$ is an anionic counterion;

W is chosen from a $(C_2$-$C_3)$alkylene and a $(C_2$-$C_3)$alkenylene chain optionally substituted with at least one $(C_1$-$C_4)$alkyl or aryl group;

$Z_1$ is chosen from a carbon atom and a nitrogen atom $N^+$ which is quaternized;

$Z_2$, $Z_3$, and $Z_4$, which may be identical or different, are chosen from a nitrogen atom, a $CR^4$ group, and a $N^+R^5$ group; with the proviso that only one quaternized nitrogen atom $N^+$ or $N^+R^5$ is present in the aromatic ring A;

$R^1$, $R^2$, and $R^4$, which may be identical or different, are chosen from a hydrogen atom, a halogen atom, a (di)

($C_1$-$C_6$)(alkyl)amino, a cyano, a hydroxyl, a (poly)halo ($C_1$-$C_6$)alkyl, an acyl($C_1$-$C_4$)(alkyl)amino, a ($C_1$-$C_6$) alkoxy, a ($C_1$-$C_6$)alkylthio, a (poly)hydroxy($C_2$-$C_6$) alkoxy, a ($C_1$-$C_6$)alkylcarbonyloxy, a ($C_1$-$C_6$) alkoxycarbonyl, a ($C_1$-$C_6$)alkylcarbonylamino, a (di) ($C_1$-$C_4$)(alkyl)aminocarbonyl, a ($C_1$-$C_6$)alkylsulfonyl ($C_1$-$C_4$)(alkyl)amino, a (di)($C_1$-$C_4$)(alkyl) aminosulfonyl group, and a ($C_1$-$C_6$)alkyl group optionally substituted with a group chosen from ($C_1$-$C_6$) alkoxy, hydroxyl, and (di)($C_1$-$C_6$)(alkyl)amino; or, when p is an integer greater than or equal to 2, two contiguous radicals $R^2$ form, together with the carbon atoms to which they are attached, a benzo ring;

$R^3$ is chosen from a hydrogen atom, an optionally substituted ($C_1$-$C_6$)alkyl group, a (di)($C_1$-$C_6$)(alkyl)amino group, an aryl group, and a heterocycloalkyl group which is optionally substituted;

$R^5$ is chosen from an optionally substituted ($C_1$-$C_6$)alkyl group and an aryl($C_1$-$C_6$)alkyl;

L is chosen from a σ bond and an optionally substituted $C_1$-$C_{20}$ divalent hydrocarbon-based chain, optionally interrupted i) with at least one divalent group or combination thereof chosen from: —N(R)—, —N$^+$(R)(R$^o$)—, An$^-$, —O—, —C(O)—, and —S(O)$_2$—, wherein R and R$^o$, which may be identical or different, are chosen from a hydrogen, a ($C_1$-$C_4$)alkyl, a hydroxy($C_1$-$C_4$)alkyl, and an amino($C_1$-$C_4$)alkyl radical, and An$^-$ is an anionic counterion, or ii) with a cationic heterocycle or cationic heteroaryl Het$^+$, An$^-$, wherein An$^-$ is an anionic counterion and Het$^+$ is chosen from a saturated or unsaturated heterocycle comprising from 5 to 10 members and a heteroaryl comprising from 5 to 10 members;

with the proviso that, when n is 2, then m is 0, and when n is 1, then m is 1.

2. The fluorescent dye according to claim 1, wherein m and n are 1.

3. The fluorescent dye according to claim 1, wherein n=2 and m=0.

4. The fluorescent dye according to claim 1, wherein unit A:

a) $Z_1$ is a quaternized nitrogen atom N$^+$, and $Z_2$, $Z_3$, and $Z_4$ are CR$^4$, or $Z_3$ and $Z_4$ are CH and $Z_2$ is chosen from a ($C_1$-$C_6$)alkylcarbonylamino and a (di)($C_1$-$C_4$)(alkyl)-aminocarbonyl group;

b) $Z_2$ is a group N$^+$R$^5$, $Z_1$ is a carbon atom, and $Z_3$ and $Z_4$ are CR$^4$;

c) $Z_4$ is a group N$^+$R$^5$, $Z_1$ is a carbon atom, and $Z_3$ and $Z_2$ are CR$^4$; or d) $Z_1$ is a quaternized nitrogen atom N$^+$, $Z_2$ and $Z_4$ are CR$^4$, and $Z_3$ is a nitrogen atom.

5. The fluorescent dye according to claim 1, wherein the dye is of formula (Ia) below:

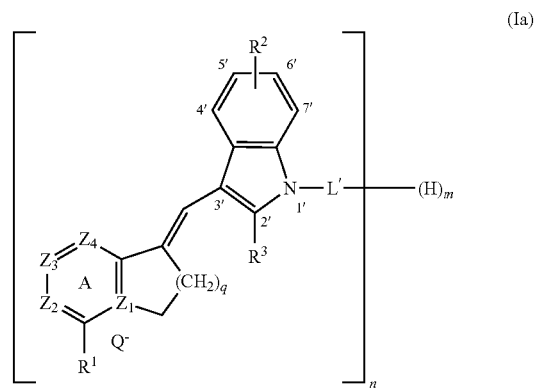

wherein:

n, m, and Q$^-$ are as defined in claim 1;

wherein unit A:

a) $Z_1$ is a quaternized nitrogen atom N$^+$, and $Z_2$, $Z_3$, and $Z_4$ are CR$^4$, or $Z_3$ and $Z_4$ are CH and $Z_2$ is chosen from a ($C_1$-$C_6$)alkylcarbonylamino and a (di)($C_1$-$C_4$) (alkyl)-aminocarbonyl group;

b) $Z_2$ is a group N$^+$R$^5$, $Z_1$ is a carbon atom, and $Z_3$ and $Z_4$ are CR$^4$;

c) $Z_4$ is a group N$^+$R$^5$, $Z_1$ is a carbon atom, and $Z_3$ and $Z_2$ are CR$^4$; or d) $Z_1$ is a quaternized nitrogen atom N$^+$, $Z_2$ and $Z_4$ are CR$^4$, and $Z_3$ is a nitrogen atom;

q is an integer ranging from 1 to 2;

$R^1$ is chosen from a hydrogen atom and a ($C_1$-$C_6$)alkyl group;

$R^2$ is absent or is chosen from a halogen atom, a ($C_1$-$C_3$) alkoxy, and a ($C_1$-$C_3$)alkoxycarbonyl group;

$R^3$ is chosen from a hydrogen atom, a ($C_1$-$C_6$)alkyl group, a phenyl group, a (di)($C_1$-$C_6$)(alkyl)amino group, and a monocyclic, 5- to 7-membered heterocycloalkyl group comprising from 1 to 3 heteroatoms chosen from oxygen and nitrogen, optionally substituted with a ($C_1$-$C_2$)alkyl group;

$R^5$ is chosen from an optionally substituted ($C_1$-$C_6$)alkyl group and an aryl($C_1$-$C_6$)alkyl;

L' is chosen from a σ bond, a ($C_2$-$C_6$)alkylene chain, and an optionally substituted ($C_1$-$C_6$)alkyl group;

with the proviso that, when n is 2, then m is 0, and when n is 1, then m is 1.

6. The fluorescent dye according to claim 1, wherein the dye is chosen from one of the following formulae:
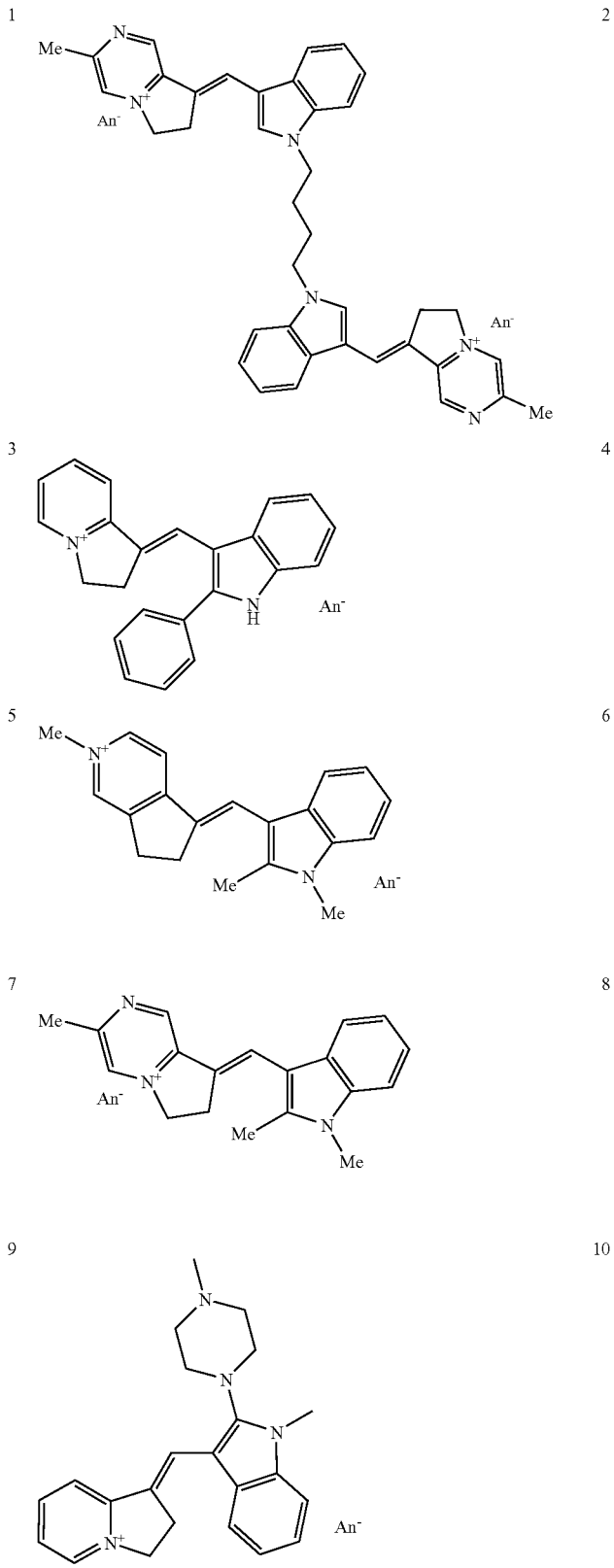

-continued
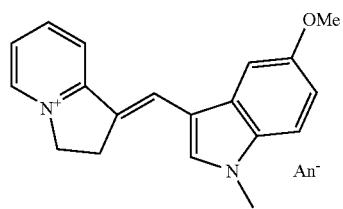
11
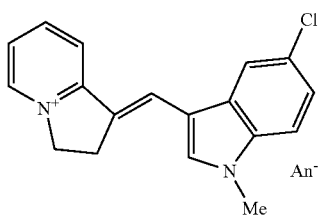
12
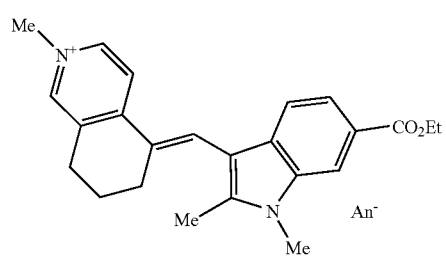
13
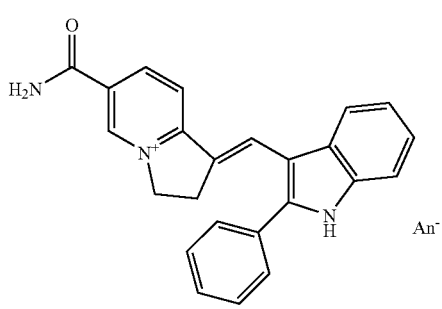
14
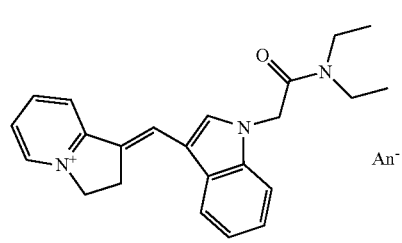
15
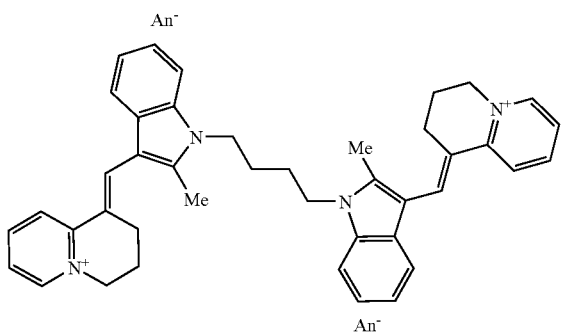
16
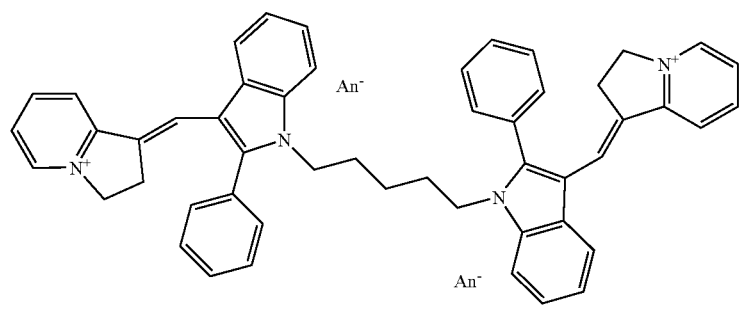
17
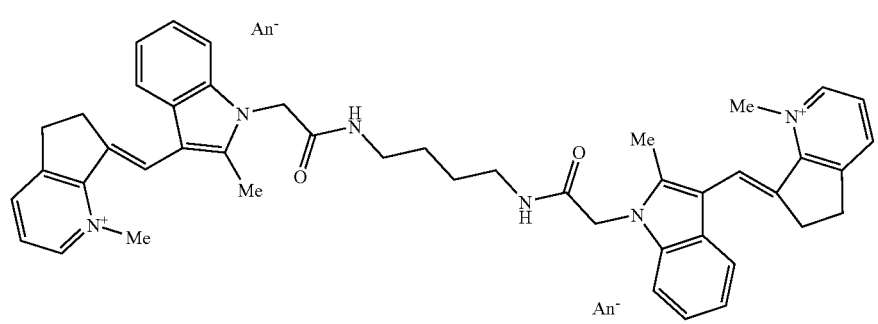
18

-continued

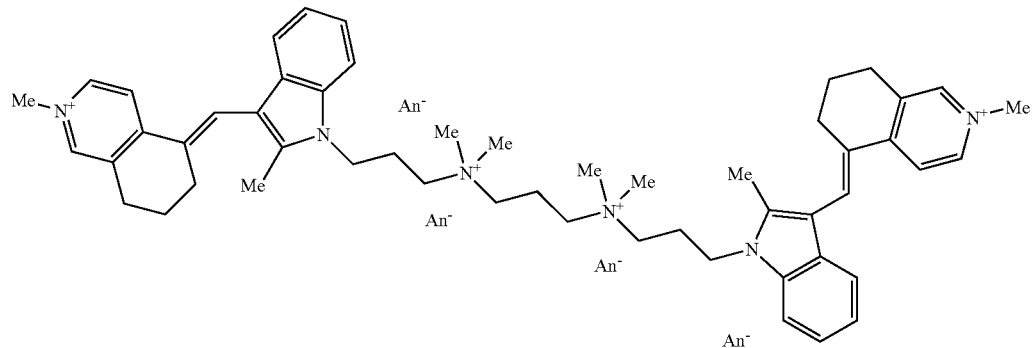

19

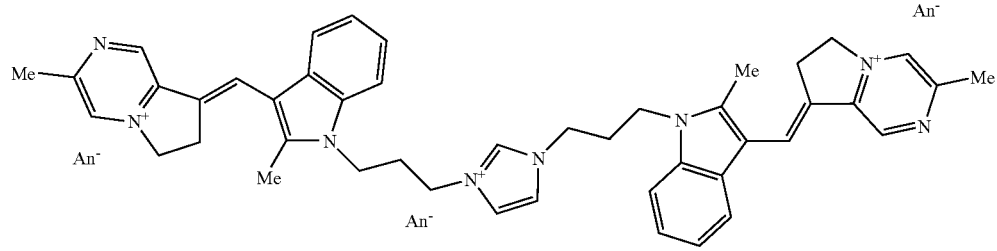

20

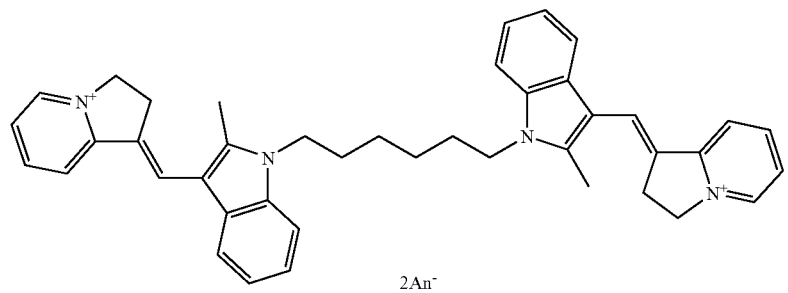

21 wherein An⁻, which may be identical or different, is an anionic counterion.

7. A dye composition comprising, in a cosmetically acceptable medium, at least one fluorescent dye of formula (I) according to claim 1.

8. The dye composition according to claim 7, wherein the at least one fluorescent dye of formula (I) is present in an amount ranging from 0.001% to 50% by weight relative to the total weight of the composition.

9. A process for dyeing keratin materials, comprising applying to the keratin materials a cosmetic dye composition comprising at least one fluorescent dye of formula (I) according to claim 1.

10. The process according to claim 9, wherein the keratin materials are dark keratin fibers.

11. The process according to claim 9, wherein the keratin materials are dark keratin fibers having a tone height of less than or equal to 6.

12. The process according to claim 9, wherein the keratin materials are lightened.

* * * * *

UNITED STATES PATENT AND TRADEMARK OFFICE
CERTIFICATE OF CORRECTION

PATENT NO.       : 7,744,658 B2                                      Page 1 of 1
APPLICATION NO.  : 12/234072
DATED            : June 29, 2010
INVENTOR(S)      : Andrew Greaves et al.

It is certified that error appears in the above-identified patent and that said Letters Patent is hereby corrected as shown below:

On the Title Page, Item (30), in the "Foreign Application Priority Data",
--07 57773" should read --0757773--.

In claim 6, in the structure for formula 21 (third structure from the top in columns 41-42),

"

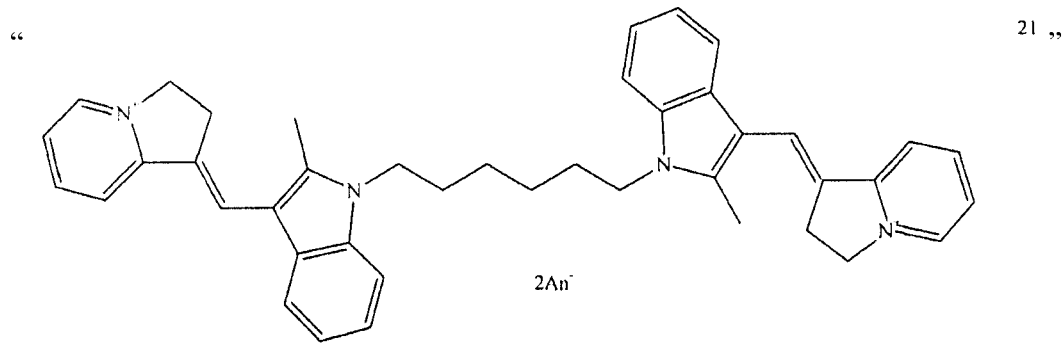

should read

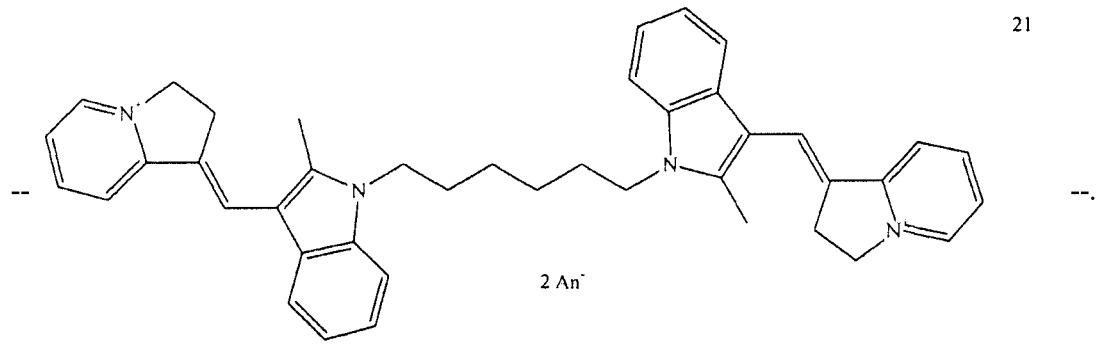

Signed and Sealed this

Twenty-third Day of November, 2010

David J. Kappos
*Director of the United States Patent and Trademark Office*